US009995803B2

(12) United States Patent
Vaughan, Jr. et al.

(10) Patent No.: US 9,995,803 B2
(45) Date of Patent: *Jun. 12, 2018

(54) AUTO-TUNE- AND-MATCH COILS FOR HUMAN WHOLE-BODY IMAGING AND METHOD

(71) Applicants: Life Services, LLC, Minneapolis, MN (US); Regents of the University of Minnesota, Minneapolis, MN (US)

(72) Inventors: J. Thomas Vaughan, Jr., Stillwater, MN (US); Charles A. Lemaire, Apple Valley, MN (US)

(73) Assignees: Regents of the University of Minnesota, Minneapolis, MN (US); Life Services, LLC, Minneapolis, MN (US)

( * ) Notice: Subject to any disclaimer, the term of this patent is extended or adjusted under 35 U.S.C. 154(b) by 919 days.

This patent is subject to a terminal disclaimer.

(21) Appl. No.: 14/508,920

(22) Filed: Oct. 7, 2014

(65) Prior Publication Data

US 2015/0123660 A1 May 7, 2015

Related U.S. Application Data

(62) Division of application No. 13/204,641, filed on Aug. 5, 2011, now Pat. No. 8,854,042.

(Continued)

(51) Int. Cl.
*G01R 33/36* (2006.01)
*G01R 33/3415* (2006.01)
(Continued)

(52) U.S. Cl.
CPC ........ *G01R 33/3628* (2013.01); *A61B 5/0044* (2013.01); *G01R 33/3415* (2013.01);
(Continued)

(58) Field of Classification Search
CPC .... G01R 33/54; G01R 33/288; G01R 33/365; G01R 33/3415; G01R 33/3453;
(Continued)

(56) References Cited

U.S. PATENT DOCUMENTS 4,682,125 A   7/1987  Harrison et al.
4,763,076 A   8/1988  Arakawa et al.
(Continued)

FOREIGN PATENT DOCUMENTS

WO   WO 2000037918   6/2000

OTHER PUBLICATIONS

Augustine, George J., "Combining patch-clamp and optical methods in brain slices", "Journal of Neuroscience Methods", Oct. 1994, pp. 163-169, vol. 54, Publisher: Elsevier.
(Continued)

*Primary Examiner* — Dixomara Vargas
(74) *Attorney, Agent, or Firm* — Quarles & Brady LLP

(57) ABSTRACT

A progressive series of five new coils is described. The first coil solves problems of transmit-field inefficiency and inhomogeneity for heart and body imaging, with a close-fitting, 16-channel TEM conformal array design with efficient shield-capacitance decoupling. The second coil progresses directly from the first with automatic tuning and matching, an innovation of huge importance for multi-channel transmit coils. The third coil combines the second, auto-tuned multi-channel transmitter with a 32-channel receiver for best transmit-efficiency, control, receive-sensitivity and parallel-imaging performance. The final two coils extend the innovative technology of the first three coils to multi-nuclear ($^{31}$P—$^{1}$H) designs to make practical human-cardiac imaging and spectroscopy possible for the first time at 7 T.

20 Claims, 22 Drawing Sheets
(11 of 22 Drawing Sheet(s) Filed in Color)

Related U.S. Application Data

(60) Provisional application No. 61/371,170, filed on Aug. 5, 2010.

(51) Int. Cl.

| | | |
|---|---|---|
| *G01R 33/54* | (2006.01) | |
| *A61B 5/00* | (2006.01) | |
| *G01R 33/28* | (2006.01) | |
| *G01R 33/345* | (2006.01) | |
| *G01R 33/565* | (2006.01) | |

(52) U.S. Cl.
CPC ............ *G01R 33/54* (2013.01); *G01R 33/288* (2013.01); *G01R 33/3453* (2013.01); *G01R 33/365* (2013.01); *G01R 33/3635* (2013.01); *G01R 33/5659* (2013.01)

(58) Field of Classification Search
CPC ............ G01R 33/3628; G01R 33/3635; G01R 33/5659; A61B 5/0044
See application file for complete search history.

(56) References Cited

U.S. PATENT DOCUMENTS

| | | | |
|---|---|---|---|
| 4,801,553 A | 1/1989 | Owen et al. | |
| 4,885,539 A | 12/1989 | Roemer et al. | |
| 4,894,589 A | 1/1990 | Borowiec | |
| 4,947,119 A | 8/1990 | Ugurbil et al. | |
| 5,075,600 A | 12/1991 | El-Hamasy et al. | |
| 5,300,888 A * | 4/1994 | Webster | G01R 33/31 324/300 |
| 5,304,930 A | 4/1994 | Crowley et al. | |
| 5,347,222 A * | 9/1994 | Fox | G01R 33/3628 324/322 |
| 5,480,482 A | 1/1996 | Novinson | |
| 5,557,247 A | 9/1996 | Vaughn, Jr. | |
| 5,610,520 A * | 3/1997 | Misic | G01R 33/3678 324/318 |
| 5,665,398 A | 9/1997 | McCormick | |
| 5,714,831 A | 2/1998 | Walker et al. | |
| 5,744,957 A | 4/1998 | Vaughan, Jr. | |
| 5,836,877 A | 11/1998 | Zavislan | |
| 5,886,596 A | 3/1999 | Vaughan, Jr. | |
| 5,903,150 A * | 5/1999 | Roznitsky | G01R 33/3657 324/318 |
| 5,908,386 A | 6/1999 | Ugurbil et al. | |
| 5,990,681 A | 11/1999 | Richard et al. | |
| 6,002,251 A | 12/1999 | Sun | |
| 6,081,120 A * | 6/2000 | Shen | G01R 33/3635 324/318 |
| 6,100,694 A | 8/2000 | Wong | |
| 6,150,816 A | 11/2000 | Srinivasan | |
| 6,300,761 B1 | 10/2001 | Hagen et al. | |
| 6,396,271 B1 | 5/2002 | Burl et al. | |
| 6,495,069 B1 | 12/2002 | Lussey et al. | |
| 6,534,983 B1 | 3/2003 | Boskamp et al. | |
| 6,538,441 B1 | 3/2003 | Watkins et al. | |
| 6,593,744 B2 | 7/2003 | Burl et al. | |
| 6,605,775 B1 | 8/2003 | Seeber et al. | |
| 6,633,161 B1 | 10/2003 | Vaughan, Jr. | |
| 6,636,037 B1 | 10/2003 | Ou-Yang | |
| 6,636,414 B2 | 10/2003 | Obert et al. | |
| 6,650,116 B2 | 11/2003 | Garwood et al. | |
| 6,664,465 B2 | 12/2003 | Seeber et al. | |
| 6,788,056 B2 | 9/2004 | Vaughan, Jr. et al. | |
| 6,788,057 B1 | 9/2004 | Petropoulos et al. | |
| 6,788,058 B1 | 9/2004 | Petropoulos et al. | |
| 6,822,448 B2 | 11/2004 | Watkins et al. | |
| 6,822,450 B2 | 11/2004 | Kline et al. | |
| 6,834,238 B1 | 12/2004 | Hochman | |
| 6,888,348 B2 | 5/2005 | Kupce | |
| 6,930,480 B1 | 8/2005 | Fijita et al. | |
| 6,946,840 B1 | 9/2005 | Zou et al. | |
| 6,958,607 B2 | 10/2005 | Vaughan, Jr. et al. | |
| 6,969,992 B2 | 11/2005 | Vaughan, Jr. et al. | |
| 6,975,115 B1 | 12/2005 | Fujita et al. | |
| 6,977,502 B1 | 12/2005 | Hertz | |
| 6,980,002 B1 | 12/2005 | Petropoulos et al. | |
| 7,023,209 B2 | 4/2006 | Zhang et al. | |
| 7,042,222 B2 | 5/2006 | Zheng et al. | |
| 7,071,693 B2 | 7/2006 | Yasuhara | |
| 7,084,631 B2 | 8/2006 | Qu et al. | |
| 7,088,104 B2 | 8/2006 | Bottomley | |
| 7,119,541 B2 | 10/2006 | Barberi | |
| 7,123,012 B2 | 10/2006 | Srinivasan | |
| 7,268,554 B2 | 9/2007 | Vaughan, Jr. | |
| 7,279,899 B2 | 10/2007 | Michaeli et al. | |
| 7,292,038 B2 | 11/2007 | Doty | |
| 7,295,870 B2 | 11/2007 | Allain et al. | |
| 7,403,006 B2 | 7/2008 | Garwood et al. | |
| 7,436,103 B2 | 10/2008 | Kawakubo et al. | |
| 7,439,736 B2 | 10/2008 | Meaney et al. | |
| 7,474,098 B2 | 1/2009 | King | |
| 7,514,926 B2 | 4/2009 | Adriany et al. | |
| 7,598,739 B2 | 10/2009 | Vaughan, Jr. et al. | |
| 7,633,293 B2 | 12/2009 | Olson et al. | |
| 7,672,650 B2 | 3/2010 | Sorrells et al. | |
| 7,701,228 B2 * | 4/2010 | Finnigan | G01R 33/3628 324/307 |
| 7,710,117 B2 | 5/2010 | Vaughan et al. | |
| 7,777,484 B2 | 8/2010 | Garwood et al. | |
| 7,800,368 B2 | 9/2010 | Vaughan et al. | |
| 8,035,384 B2 | 10/2011 | Saha | |
| 8,093,900 B2 | 1/2012 | Bennett | |
| 8,093,978 B2 | 1/2012 | Kawarai et al. | |
| 8,193,809 B2 | 6/2012 | Akgun et al. | |
| 8,217,653 B2 | 7/2012 | Vaughan et al. | |
| 8,222,796 B2 | 7/2012 | Bhaskaran et al. | |
| 8,299,681 B2 | 10/2012 | Snyder et al. | |
| 8,380,266 B2 | 2/2013 | Vaughan, Jr. et al. | |
| 8,674,695 B2 | 3/2014 | Wiggins | |
| 8,788,044 B2 | 7/2014 | John | |
| 8,854,042 B2 * | 10/2014 | Vaughan, Jr. | G01R 33/3415 324/318 |
| 9,320,452 B2 | 4/2016 | Garwood et al. | |
| 2003/0091980 A1 | 5/2003 | Lynch et al. | |
| 2003/0206019 A1 | 11/2003 | Boskamp | |
| 2005/0264291 A1 | 12/2005 | Vaughan et al. | |
| 2006/0001426 A1 | 1/2006 | Vaughan et al. | |
| 2006/0279284 A1 | 12/2006 | Vaughan, Jr. | |
| 2007/0236490 A1 | 10/2007 | Casteele et al. | |
| 2008/0180101 A1 | 7/2008 | Bradshaw et al. | |
| 2009/0134965 A1 | 5/2009 | Lemdiasov et al. | |
| 2009/0264733 A1 | 10/2009 | Corum et al. | |
| 2013/0106416 A1 | 5/2013 | Morich et al. | |

OTHER PUBLICATIONS

Cho, Y.K., et al., "Noninvasive measurements of transmural myocardial metabolites using 3-D (31)P NMR spectroscopy.", "Am J Physiology", Jan. 2001, pp. H489-H497, vol. 280, No. 1.

Nelder, J.A., et al., "A simplex method for function minimization", "Comput J.", 1965, pp. 308-313, vol. 7, No. 4.

Roemer, et al., "The NMR Phased Array", "Magnetic Resonance in Medicine", Nov. 1990, pp. 192-225, vol. 16, No. 2.

Sung K., et al., "B1+ Compensation in 3T Cardiac Imaging Using Short 2DRF Pulses", "Magnetic Resonance in Medicine", Mar. 2008, pp. 441-446, vol. 59, No. 3.

Vaughan, J.T., et al., "Clinical Imaging at 7T with a 16 Channel Whole Body Coil and 32 Receive Channels.", "Proceedings 17th Scientific Meeting, International Society for Magnetic Resonance in Medicine", Apr. 2009, pp. 392.

Wiggins, et al., "96-Channel Receive-Only Head Coil for 3 Tesla: Design Optimization and Evaluation", "Magn. Reson. Med.", Sep. 2009, pp. 754-762, vol. 62, No. 3.

* cited by examiner $$M = \frac{\Phi_{21}}{I_1} =$$

$$\frac{\mu_0}{4\pi} \iint \int \mathbf{J}_{x=L} [\mathbf{J}_{x=L,z}\cdot\hat{z}\left(\frac{j\beta}{r'} + \frac{1}{r'^2}\right)e^{-j\beta r'} + \frac{1}{r'^2}e^{-j\beta r'}\frac{x-x_0}{r'}]dy_0 dz_0 \int dx dz$$

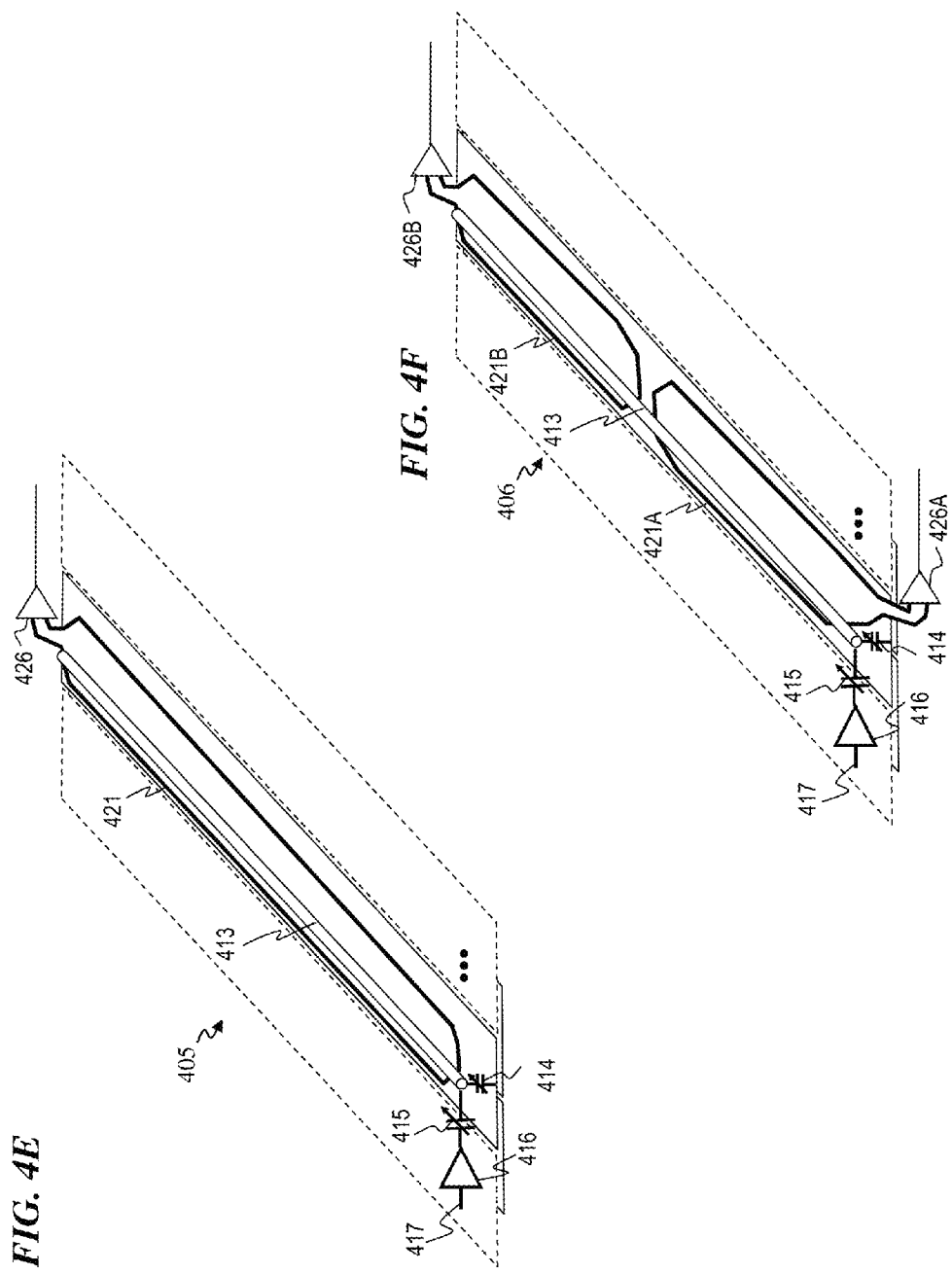

1000

AUTO-TUNE- AND-MATCH COILS FOR HUMAN WHOLE-BODY IMAGING AND METHOD

CROSS-REFERENCE TO RELATED APPLICATIONS

This application is a divisional of U.S. patent application Ser. No. 13/204,641, filed Aug. 5, 2011 and titled "Method and coils for human whole-body imaging at 7 T," (which issued as U.S. Pat. No. 8,854,042 on Oct. 7, 2014), which claims priority benefit, under 35 U.S.C. § 119(e), of U.S. Provisional Patent Application No. 61/371,170, filed on Aug. 5, 2010 and titled "Coils for human whole-body imaging at 7T," each of which is incorporated herein by reference in its entirety. This application is related to U.S. patent application Ser. No. 12/719,841, filed Mar. 8, 2010 and titled "Remotely adjustable reactive and resistive electrical elements and method" (which issued as U.S. Pat. No. 8,299,681 on Oct. 30, 2012), which is incorporated herein by reference in its entirety.

FIELD OF THE INVENTION

This invention relates to the field of magnetic-resonance imaging (MRI) and magnetic-resonance spectroscopy (MRS), and more specifically to a method and apparatus for transmitting (TX) and receiving (RX) radio-frequency (RF) signals suitable for MRI and/or MRS.

BACKGROUND OF THE INVENTION

United States Patent Application Publication US 2006/0279284 by J. Thomas Vaughan Jr. published Dec. 14, 2006, titled "Wirelessly coupled magnetic resonance coil," and is incorporated herein by reference. In this document Vaughan describes a radio frequency magnetic coil is coupled to a wireless communication circuit. The wireless communication circuit allows control or monitoring of individual channels or other functions of a coil.

United States Patent Application Publication US 2009/0237077 (which issued as U.S. Pat. No. 8,217,653 on Jul. 10, 2012) by J. Thomas Vaughan published on Sep. 24, 2009, titled "RF COIL FOR IMAGING SYSTEMS AND METHODS OF OPERATION," is incorporated herein by reference. This publication describes an RF coil system for magnetic resonance applications that includes a multi-channel RF coil transceiver and a multi-channel RF coil. The RF coil system is structured for reconfiguration among a plurality of operational modes.

United States Patent Application Publication US 2009/0115417 (which issued as U.S. Pat. No. 8,193,809 on Jun. 5, 2012) by Akgun, et al. published on May 7, 2009, titled "Three dimensional RF coil structures for field profiling," is incorporated herein by reference. This publication details that in one illustrative embodiment, a radio frequency (RF) coil is disclosed. The RF coil may include a plurality of transmission line elements, wherein at least one of the plurality of transmission line elements may have at least one dimension different than a dimension of another one of the plurality of transmission line elements. In some cases, each of the transmission line elements may include a signal line conductor and a ground plane conductor separated by a dielectric.

PCT Patent Application PCT/US2009/060841 was filed by Vaughan et al. on Oct. 15, 2009, is titled "COIL ELEMENT DECOUPLING FOR MRI," and is incorporated herein by reference. In this document, Vaughan et al. describe an RF coil adjacent an imaging region includes a plurality of conducting coil elements, with each conducting coil element including a proximal portion and a distal portion. The RF coil also includes a capacitance between the distal portions of the at least two conducting coil elements. A mutual coupling inductance between at least two conducting coil elements of the plurality of conducting coil elements is substantially cancelled by the capacitance between the distal portions of the at least two conducting coil elements.

U.S. Pat. No. 7,268,554 issued to Vaughan on Sep. 11, 2007, titled "RF coil for imaging system," is incorporated herein by reference. In this patent, an RF coil suitable for use in imaging systems is described, which coil has a dielectric filled cavity formed by a surrounding conducting enclosure, the conducting enclosure preferably being patterned to form continuous electrical paths around the cavity, each of which paths may be tuned to a selected resonant frequency. The patterning breaks up any currents induced in the coil and shortens path lengths to permit higher frequency, and thus higher field strength operation. The invention also includes improved mechanisms for tuning the resonant frequency of the paths, for selectively detuning the paths, for applying signal to the coil, for shortening the length of the coil and for controlling the field profile of the coil and the delivery of field to the object to the image.

U.S. Pat. No. 6,633,161 issued to Vaughan, Jr. on Oct. 14, 2003, titled "RF coil for imaging system," is incorporated herein by reference. In this patent, an RF coil suitable for use in imaging systems is provided which coil has a dielectric filled cavity formed by a surrounding conducting enclosure, the conducting enclosure preferably being patterned to form continuous electrical paths around the cavity, each of which paths may be tuned to a selected resonant frequency. The patterning breaks up any currents induced in the coil and shortens path lengths to permit higher frequency, and thus higher field strength operation. The invention also includes improved mechanisms for tuning the resonant frequency of the paths, for selectively detuning the paths, for applying signal to the coil, for shortening the length of the coil and for controlling the field profile of the coil and the delivery of field to the object to the image.

U.S. Pat. No. 5,557,247 issued to Vaughan, Jr. on Sep. 17, 1996, titled "Radio frequency volume coils for imaging and spectroscopy," is incorporated herein by reference. This patent describes a distributed impedance circuit MR coil design comprised of a transmission line tunable cavity resonator which is well suited for but not limited to use at high frequencies and for large volumes such as in high field (e.g., 4.1 tesla) clinical MR applications. The distributed circuit transmission line resonator is designed for high frequency, large conductive volume applications where conventional lumped element coil designs fail. A resonant coaxial cavity is variably tuned to the Larmor frequency of interest by tunable transmission line elements. The resonator is effective for large head and body sized volumes, high efficiencies, and broad tuning ranges to frequencies of 500 MHz. The $B_1$ homogeneity of the resonator is a function of the electromagnetic properties of the load itself. Maxwell's equations for the fully time-dependent $B_1$ field predicts "coil" homogeneity with finite-element models of anatomic structure. Coil design and construction, and methods of quadrature driving and double tuning the transmission line resonator, are set forth.

U.S. Pat. No. 5,744,957 issued to Vaughan, Jr. on Apr. 28, 1998, titled "Cavity resonator for NMR systems," is incorporated herein by reference. In this patent, a cavity resonator is disclosed for use in nuclear magnetic resonance (NMR) systems. The resonator has a housing defining a cavity having a selected length and cross-sectional shape. A layer of electrically conductive material is provided around at least a portion of the housing enclosing a dielectric material (air, gasses, Teflon®, etc.) and the cavity is energized at a Larmor radio frequency useful for NMR systems. The cavity, i.e., a volume enclosed by conductive walls, furthermore, is dimensioned to resonate at the selected radio frequency to thereby generate an alternating magnetic field through the cavity. An opening in the housing is adapted to be placed adjacent an object to be analyzed.

U.S. Pat. No. 5,886,596 issued to Vaughan, Jr. on Mar. 23, 1999, titled "Radio frequency volume coils for imaging and spectroscopy," is incorporated herein by reference. This patent describes an electromagnetic shield for an NMR radio frequency coil designed to resonate at a selected Larmor frequency. The shield includes an electrically conductive layer surrounding the coil. This electrically conductive layer has a thickness substantially the same as one skin depth at the selected Larmor frequency. As such, the conductive layer efficiently conducts radio frequency currents at the selected Larmor frequency thereby conducting and containing the radio frequency coils at the selected Larmor frequency within the coil. Simultaneously, an electrically conductive layer, due to its thinness, very inefficiently conducts eddy currents of the type induced by the lower frequency DC gradient current switching transients the gradients are utilized to magnetically localize an image slice or volume. Consequently, the conductive layer simultaneously attenuates low frequency eddy current propagation of the type induced by the switching field gradient currents in the NMR application, and therefore does not substantially shield or affect the gradient fields across the coil.

U.S. Pat. No. 7,800,368 issued to Vaughan, et al. on Sep. 21, 2010, titled "High field magnetic resonance," is incorporated herein by reference. In this patent, a magnetic resonance system is disclosed. The system includes a transceiver having a multichannel receiver and a multichannel transmitter, where each channel of the transmitter is configured for independent selection of frequency, phase, time, space, and magnitude, and each channel of the receiver is configured for independent selection of space, time, frequency, phase and gain. The system also includes a magnetic resonance coil having a plurality of current elements, with each element coupled in one to one relation with a channel of the receiver and a channel of the transmitter. The system further includes a processor coupled to the transceiver, such that the processor is configured to execute instructions to control a current in each element and to perform a non-linear algorithm to shim the coil.

U.S. Pat. No. 6,788,056 issued to Vaughan, et al. on Sep. 7, 2004, titled "Radio frequency magnetic field unit with aperature [sic]," and is incorporated herein by reference. In this document, Vaughan et al. describe an apparatus comprises a radio frequency magnetic field unit to generate a desired magnetic field. In one embodiment, the radio frequency magnetic field unit includes a first aperture that is substantially unobstructed and a second aperture contiguous to the first aperture. In an alternative embodiment, the radio frequency magnetic field unit includes a first side aperture, a second side aperture and one or more end apertures. In one embodiment of a method, a current element is removed from a radio frequency magnetic field unit to form a magnetic field unit having an aperture. In an alternative embodiment, two current elements located opposite from one another in a radio frequency magnetic field unit are removed to form a magnetic filed unit having a first side aperture and a second side aperture.

U.S. Pat. No. 6,958,607 issued to Vaughan, et al. on Oct. 25, 2005, titled "Assymetric [sic] radio frequency transmission line array," is incorporated herein by reference. In this document, Vaughan et al. describe an apparatus comprises a radio frequency magnetic field unit to generate a desired magnetic field. In one embodiment, the radio frequency magnetic field unit includes a first aperture that is substantially unobstructed and a second aperture contiguous to the first aperture. In an alternative embodiment, the radio frequency magnetic field unit includes a first side aperture, a second side aperture and one or more end apertures. In one embodiment of a method, a current element is removed from a radio frequency magnetic field unit to form a magnetic field unit having an aperture. In an alternative embodiment, two current elements located opposite from one another in a radio frequency magnetic field unit are removed to form a magnetic filed unit having a first side aperture and a second side aperture.

U.S. Pat. No. 7,023,209 issued to Zhang, et al. on Apr. 4, 2006 titled "Method and apparatus for magnetic resonance imaging and spectroscopy using microstrip transmission line coils," and is incorporated herein by reference. In this document, Zhang et al. describe an apparatus and method for MRI imaging using a coil constructed of microstrip transmission line (MTL coil) are disclosed. In one method, a target is positioned to be imaged within the field of a main magnetic field of a magnet resonance imaging (MRI) system, a MTL coil is positioned proximate the target, and a MRI image is obtained using the main magnet and the MTL coil. In another embodiment, the MRI coil is used for spectroscopy. MRI imaging and spectroscopy coils are formed using microstrip transmission line. These MTL coils have the advantageous property of good performance while occupying a relatively small space, thus allowing MTL coils to be used inside restricted areas more easily than some other prior art coils. In addition, the MTL coils are relatively simple to construct of inexpensive components and thus relatively inexpensive compared to other designs. Further, the MTL coils of the present invention can be readily formed in a wide variety of coil configurations, and used in a wide variety of ways. Further, while the MTL coils of the present invention work well at high field strengths and frequencies, they also work at low frequencies and in low field strengths as well.

U.S. Pat. No. 6,969,992 issued to Vaughan, et al. on Nov. 29, 2005, titled "Parallel transceiver for nuclear magnetic resonance system," is incorporated herein by reference. This patent describes an excitation and detection circuit having individually controllable elements for use with a multi-element radio frequency coil. Characteristics of the driving signal, including, for example, the phase, amplitude, frequency and timing, from each element of the circuit is separately controllable using small signals. Negative feedback for the driving signal associated with each coil element is derived from a receiver coupled to that coil element.

U.S. Pat. No. 7,710,117 issued to Vaughan, et al. on May 4, 2010, titled "Multi-current elements for magnetic resonance radio frequency coils," is incorporated herein by reference. This patent describes a current unit having two or more current paths that allow control of magnitude, phase, time, frequency and position of each of element in a radio frequency coil. For each current element, the current can be adjusted as to a phase angle, frequency and magnitude. Multiple current paths of a current unit can be used for targeting multiple spatial domains or strategic combinations of the fields generated/detected by combination of elements for targeting a single domain in magnitude, phase, time, space and frequency.

U.S. Pat. No. 7,514,926 issued to Adriany, et al. on Apr. 7, 2009, titled "Spatially reconfigurable magnetic resonance coil," is incorporated herein by reference. This patent discusses, among other things, a system and method for a coil having a plurality of resonant elements and an adjustable frame. A position of at least one resonant element can be adjusted relative to at least one other resonant element. A variable impedance is coupled to adjacent resonant elements and the impedance varies as a function of a separation distance. Cables are coupled to each resonant element and are gathered at a junction in a particular manner.

U.S. Pat. No. 7,598,739 issued to Vaughan, Jr., et al. on Oct. 6, 2009, titled "Radio frequency gradient, shim and parallel imaging coil," is incorporated herein by reference. This patent describes a plurality of linear current elements that are configured about a specimen to be imaged. A current in each current element is controlled independent of a current in other current elements to select a gradient and to provide radio frequency shimming. Each current element is driven by a separate channel of a transmitter and connected to a separate channel of a multi-channel receiver. The impedance, and therefore, the current, in each current element is controlled mechanically or electrically.

U.S. Pat. No. 7,633,293 issued to Olson, et al. on Dec. 15, 2009, titled "Radio frequency field localization for magnetic resonance," is incorporated herein by reference. This patent describes that technology for controlling non-uniformity in the $B_1$ field includes selecting the phase, magnitude, frequency, time, or spatial relationship among various elements of a multi-channel excitation coil in order to control the radio frequency (RF) power emanating from the coil antenna elements. Non-uniformity can be used to steer a constructively interfering $B_1$ field node to spatially correlate with an anatomic region of interest. A convex (quadratically constrained quadratic problem) formulation of the $B_1$ localization problem can be used to select parameters for exciting the coil. Localization can be used in simulated Finite Difference Time Domain $B_1$ field human head distributions and human head phantom measurement.

U.S. Pat. No. 6,495,069 issued Dec. 17, 2002 to Lussey et al. titled "Polymer composition," is incorporated herein by reference. Lussey et al. describe a polymer composition comprises at least one substantially non-conductive polymer and at least one electrically conductive filler and in the form of granules. Their elastomer material was proposed for devices for controlling or switching electric current, to avoid or limit disadvantages such as the generation of transients and sparks which are associated with the actuation of conventional mechanical switches. They described an electrical conductor composite providing conduction when subjected to mechanical stress or electrostatic charge but electrically insulating when quiescent comprising a granular composition each granule of which comprises at least one substantially non-conductive polymer and at least one electrically conductive filler and is electrically insulating when quiescent but conductive when subjected to mechanical stress. They did not propose a means for electrically activating such switches.

There is a long-felt need for components having resistance, inductance, and/or capacitance values that are variable under electrical control and are compatible with being operated in extremely high electromagnetic fields.

SUMMARY OF THE INVENTION

According to the National Heart Lung and Blood Institute, more Americans die from cardiovascular diseases than any other cause. Approximately 25% of all Americans have one or more cardiovascular diseases (CVDs). With more than 1.2 million deaths per year, nearly one out of every two American adults dies of CVDs. Highly sensitive detection is critical to biomedical science, and to diagnoses and successful treatments for these diseases. MRI/MRS at 7 T have great potential as tools for imaging and spectroscopic detection of cardiovascular diseases. While forty 7-T MRI systems are installed in luminary labs around the world, there were no means available for practical 7-T cardiac MRI and MRS. This problem is solved by the new technology and methods required for applying MR techniques to the heart. A progressive series of five new coils is described. The first coil solves problems of transmit-field inefficiency and inhomogeneity for heart and body imaging, with a close-fitting, 16-channel TEM (transverse electrical-magnetic field) conformal-array design with efficient shield-capacitance decoupling. The second coil progresses directly from the first with automatic tuning and matching, an innovation of huge importance for multi-channel transmit coils. The third coil combines the auto-tuned multi-channel transmitter of the second coil with a 32-channel receiver for best transmit-efficiency, control, receive-sensitivity and parallel-imaging performance. The final two coils extend the innovative technology of the first three coils to multi-nuclear ($^{31}P$—$^1H$) designs to make practical human-cardiac imaging and spectroscopy possible for the first time at 7 T. Other advantages will become apparent to those skilled in the art upon reading the following detailed description of various embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4E shows a perspective schematic view of a transmit-receive element 405 according to some embodiments of the present invention.

FIG. 4F shows a perspective schematic view of a transmit-receive element 406 according to some embodiments of the present invention.

FIG. 8 (which includes FIGS. 8A and 8B) shows a sixteen-channel TEM array fully packaged in place on a subject (left) and open with both halves visible (right) (FIG. 8A rendering of the TEM array with one part above and one part below the body.

DESCRIPTION OF PREFERRED EMBODIMENTS

Figure 1:
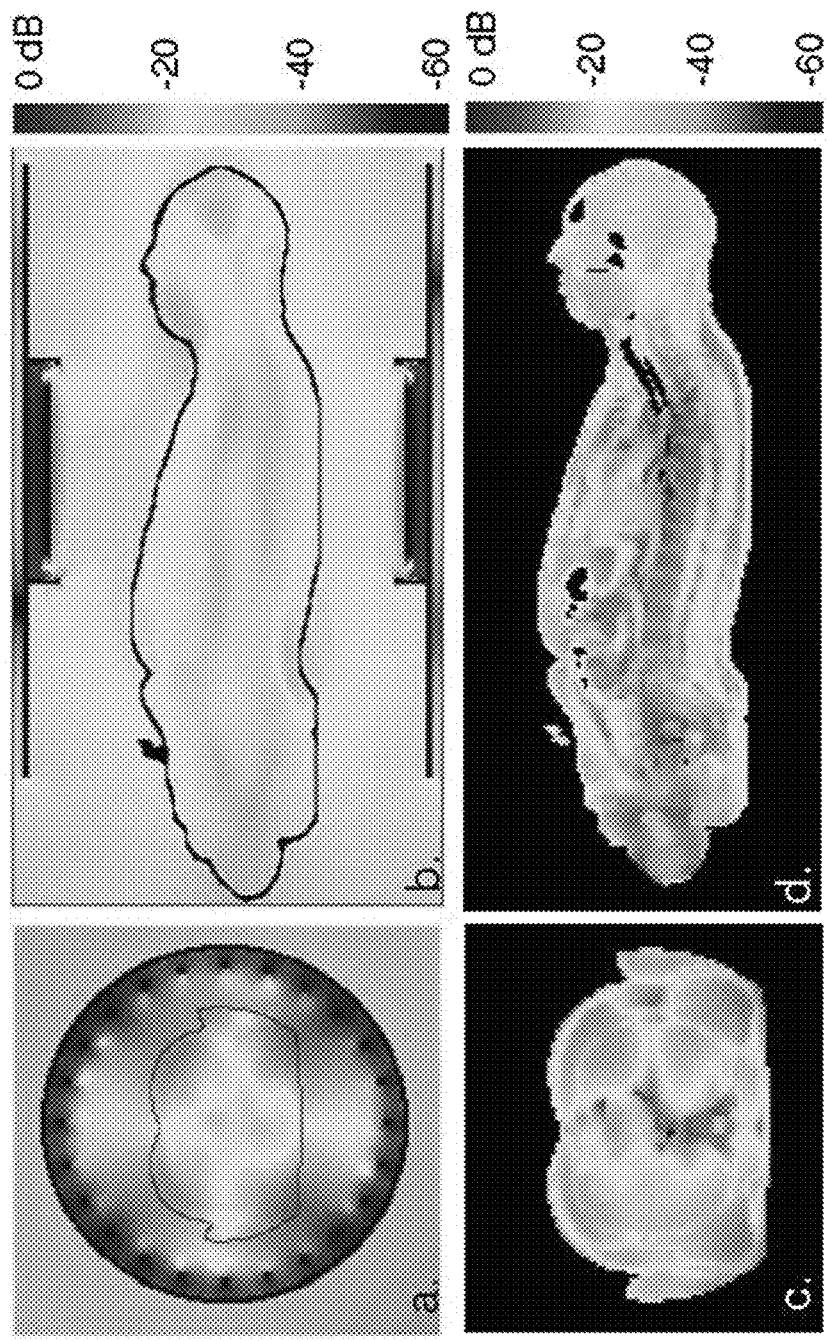
FIG. 1 shows the destructive-interference patterns when a circularly polarized body coil is used for excitation in the thorax at 7T.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

1. EMBODIMENTS

In some embodiments, the present invention includes a series of RF coils that make practical 7-tesla (7-T) cardiac and whole-body imaging and spectroscopy possible. This taps the inherent potential of 7 T already proven with neuroimaging for non-invasive observation of the living human heart in health, disease, and therapeutic intervention. There is no engineering target in medical imaging more challenging than imaging the human heart in vivo at 7 T. This is perhaps why the forty 7-T research systems in the world are dedicated primarily to head imaging. The most significant challenges to cardiac imaging are related to radio-frequency (RF) field propagation and loss in the body. At 7 T the Larmor wavelength in the body, specifically in high-water-content tissues, is approximately 12 cm. This reduced wavelength results in RF magnetic field ($B_1$) interference patterns that cause severe image inhomogeneity when conventional circularly polarized body coils are used. RF magnetic field "$B_1$" interference patterns of 12-cm Larmor wavelengths in high-water-content human tissues result in severe image inhomogeneity when conventional circularly polarized body coils are used. If these highly inductive, lumped element, birdcage body coils could even be tuned to 300 MHz, they would be very inefficient. At 12-cm wavelengths, electromagnetic (EM) energy is deposited at high Specific Absorption Rates (SAR) with consequences of increased RF heating and attenuated signal-to-noise ratios (SNR). In electrical dimensions, the human body at 300 MHz is the largest load ever imaged by MRI. Dimensional differences between bodies and body placement within a coil require per-subject tune and match adjustments. Multi-nuclear signal excitation and acquisition add another significant level of complexity. There are additional problems with imaging a heart at 7 T, including dynamic susceptibility shifts, magnetohydrodynamic (MHD) related artifacts in the vector cardiogram (VCG), and new relaxation constants to be incorporated into new pulse sequences. Ergonomics and human comfort are considerations as well. Herein, we solve the RF-technology-related problems and thereby render for the first time a practical 7-T cardiac imager. This achievement will leverage the remaining solutions and refinements through new pulse protocol design and applications development. For this purpose, we have joined forces with the University of Oxford to benefit from their strengths in cardiac imaging research and diagnostics. Together, we will develop and discover the potential of 7-T cardiac MRI and MRS for biomedical research. The present invention includes a series of embodiments of RF coils for 7-T cardiac imaging and spectroscopy that each embodies uniquely innovative coils listed as embodiments. These embodiments include:

Embodiment 1

16-Channel Transceiver Coil

Sixteen transmit channels are provided for maximizing $B_1$ transmit efficiency while minimizing SAR through $B_1$ shimming. Sixteen receive channels are required for parallel acceleration. Key innovations in this Embodiment include the first use of shield capacitance decoupling in a TEM (transverse electrical-magnetic field) array and interface provisions for Embodiment 2.

Embodiment 2

Auto-Tuned and Matched Transceiver Coil

In prior-art coils, every channel of a multi-channel transmit or transceiver coil must be manually tuned and matched before every study, rendering these coils impractical for research use and unusable for clinical diagnostics. This problem is solved by this unique, automated tune-and-match system of this added to Embodiment 1.

Embodiment 3

Auto-Tuned, 16-Channel Transmit Coil with Integrated 32-Channel Receiver

In clinical coils for lower fields, the transmit and receive functions are separated in body imaging. Transmit coils are used to excite a uniform field. Receive coils are used to maximize sensitivity. High-count receiver elements maximize parallel imaging performance. This innovative design will accomplish all three, and include multi-channel transmit $B_1$ shimming with automated tune and match.

Embodiment 4

Auto-Tuned, Multinuclear Transceiver Coil

High SNR and spectral resolution at 7 T compel cardiac-spectroscopy development. The double-tuned coil of this embodiment 4 with autotuning meets the needs of this environment.

Embodiment 5

Auto-Tuned, Multinuclear Transmit Coil with Integrated Receiver

In this complex, double-tuned ($^{31}$P—$^1$H) coil, transmit and receive components are separated and the receive array element count is doubled, for the same reasons as in Embodiment 3.

MRI/MRS at 7 T may augment or replace other investigational and diagnostics methods. Underscoring this belief, the NHLBI has issued at least fourteen program announcements over the last decade specifically requesting grant applications for NMR-based investigation of CVDs. The National Center for Research Resources (NCRR) and National Institute of Biomedical Imaging and Bioengineering (NIBIB) have also broadly supported the development of MR methods and technology for cardiovascular research.

To realize the compelling potential for 7-T cardiac MR diagnosis, the tools and methods must first be developed. There are currently no commercially available methods or tools for 7-T cardiac MR diagnosis. Not waiting for industry, we have designed, built and employed new technology coils, $B_1$ shimming methods, parallel-imaging (including parallel-transmit) techniques, and a 16-channel transceiver. Based on preliminary results from human studies facilitated by these new tools, the signal-to-noise ratio required for enhanced cardiovascular disease detection sensitivity can be improved by a factor of five compared to conventional prior-art 1.5-T MRI capabilities, and more than twice the SNR of 3-T platforms. Parallel-imaging improvements with field strength promise further increases in SNR and temporal resolution (reference 1). According to our SAR modeling and animal RF-heating experiments, these performance gains can be obtained within safe SAR and thermal limitations (references 2-4).

If cardiac imaging and spectroscopy are to benefit from 7-T NMR, then the engineering developments of this invention are necessary. There are many compelling and well-supported scientific arguments for employing the imaging signal, speed, contrast, and spatial and spectral resolution power of 7T for human biomedical research. The fact that forty 7-T whole-body systems exist today, and that even in recessionary times this number is rapidly growing, underscores the vote from the scientific community for the need of 7-T MR in the biomedical lab. Due to RF technology limitations however, the vast majority of 7-T applications are limited to head imaging. The new RF technology described herein will extend the benefits of 7 T to cardiac research, and to the other organs of the human trunk as well. Without the new technology, the 7-T system and associated significant resources and funding will remain for patient's heads only.

This application provides the critical innovation in technology and methodology to take 7-T cardiac imaging beyond a demonstration of feasibility. A short list of some innovations follows.

Cardiac Imaging at 7 T:

Cardiac imaging and spectroscopy of the human heart at 7 T is innovative. Cardiac imaging is still at the feasibility-demonstration stage (references 5, 6, 7, 8, 9). Cardiac spectroscopy for humans at 7 T is nonexistent. The innovation provided by the present invention helps cardiac imaging and spectroscopy become useful as a biomedical research or clinical diagnostic tool. The most significant challenge for 7-T cardiac imaging comes from the destructive interference patterns due to the 12-cm excitation wavelengths in the thorax.

FIG. 1 shows the destructive interference patterns when a circularly polarized body coil is used for excitation in the thorax at 7 T (reference 4). (It should be noted that this is the method used for cardiac imaging, with success, in existing 1.5-T and 3-T systems.) Due to this problem and other technological challenges, 7-T systems do not have body coils and are not configured for body imaging of any sort. Note that the regions of destructive interference are strongest, to −40 dB, in the heart, resulting in very low or no signal from the heart. Conventional efforts of compensating by increasing RF transmit power quickly reach SAR limits without correcting the problem. $B_1$ shimming and the technology to execute it was invented by our team to mitigate this problem, first for 7-T and 9.4-T head imaging. (Van de Moortele, 2006 #146; Van de Moortele, 2005 #130; Vaughan, 2006 #286.) $B_1$ shimming, based on choosing the phase, magnitude, and/or temporal dimensions of current waveforms on independent transmit elements to generate constructively interfering waveforms at the region of interest (ROI) to optimize RF-dependent parameters and to minimize SAR, has also been demonstrated for successful human heart imaging at 4 T and 7 T. (Vaughan, 2004 #284; Snyder, 2009 #311.)

FIG. 1 shows Maxwell models of $B_1$ and SAR contours generated by a body coil in the human body at 7 T. Figures a and b show relative $B_1$ equipotentials, T/m (dB) in centerline transverse and sagittal planes. Figures c and d show SAR, W/kg (dB) equipotentials in the same planes, respectively. The body coil modeled measured i.d.=57.5 cm, o.d.=62.5 cm, element length=33 cm, cavity length=100 cm. This 32-element body coil was driven at four ports (45°, 135°, 225°, 315°) referenced to 0 degrees at the bottom of the coil. The $B_1$ field generated in the coil was circularly polarized and uniform in the unloaded state.

Multi-Channel Transmission Line "TEM" Arrays

A cardiac coil should include an array of electrically short, highly distributed, resonant elements for highest efficiency at 300 MHz. The array should be composed of multiple, independently driven transmit elements surrounding the heart for $B_1^+$ field control and coverage. To further maximize efficiency, the transmit coil elements should be backed by a cavity wall or shield of a slotted, double-sided skin-depth foil design to attenuate switched gradient-induced currents. Multiple, small receive elements, which may be the same as transmit elements with transmit and receive functions separated in time by a transmit-receive switch, are required for sensitivity, field-of-view (FOV) coverage and for faster, parallel acquisition. To further maximize transmit and receive efficiency, the transmit and receive elements should be closely fitted to the thorax while allowing a couple of centimeters for electrical insulation and ergonomic padding. All of these requirements for a cardiac coil are met in the prototype coil 219 shown in FIG. 2A. A pair of these multi-channel TEM coils was used to acquire the cardiac-imaging feasibility data shown in FIG. 16. Similar coils are described in U.S. Pat. No. 7,710,117 titled "Multi-current elements for magnetic resonance radio frequency coils," which is incorporated herein by reference.

Figure 2A:
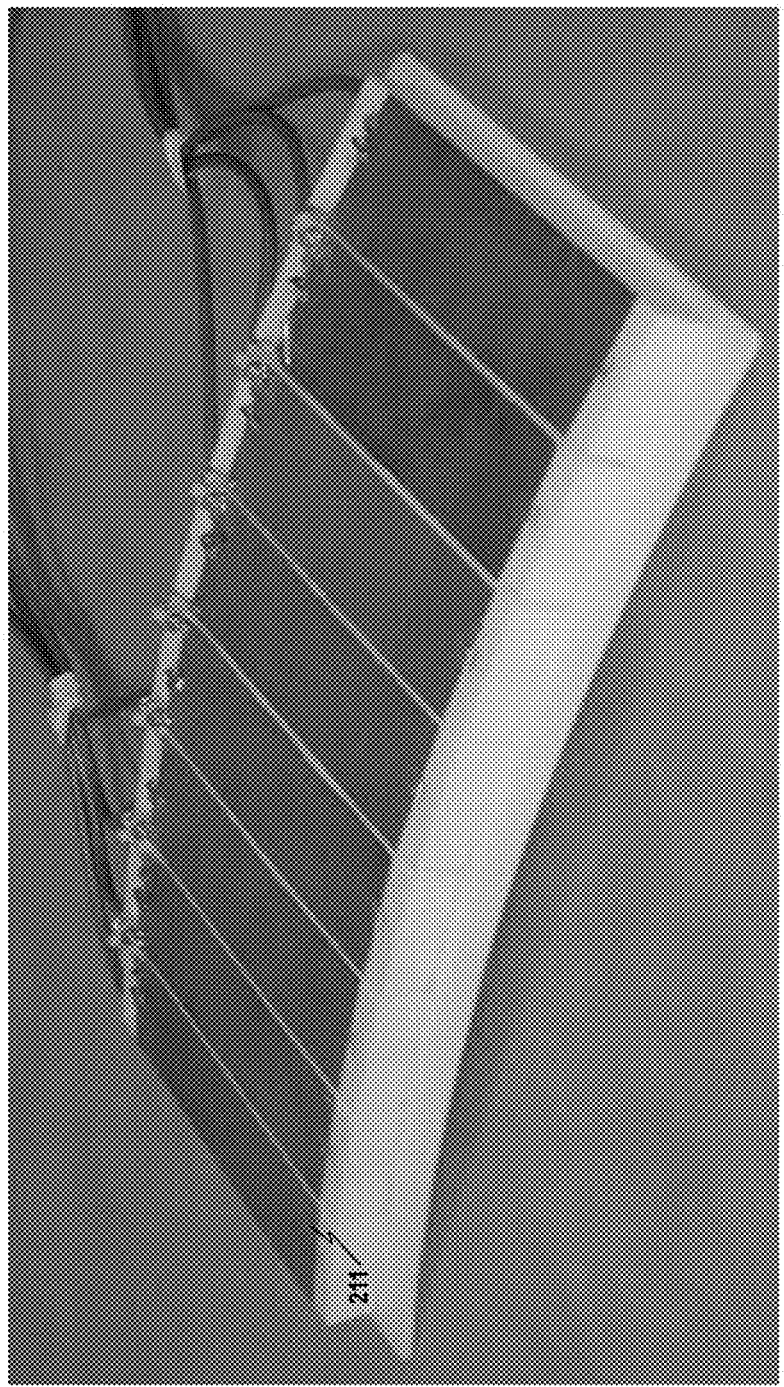
FIG. 2A is a photograph of a conventional cardiac coil 219. Similar coils are described in U.S. Pat. No. 7,710,117 titled "Multi-current elements for magnetic resonance radio frequency coils," which is incorporated herein by reference.

The prototype coil 219 shown in FIG. 2a would not be useful for most 7-T research sites, since it must be manually tuned and matched in place on each and every subject inside the magnet bore. For the 16-element coil, 32 tune-and-match operations must be performed for each study, by means of long tuning rods extending from the back of the magnet, beneath the head and over the face of the subject. (For example, to a manually-adjustable capacitor connected serially between the end of each cable and the end of each transmit element (not visible here) and to a manually-adjustable capacitor connected in parallel between the end of each cable and the end of each shield element 211.) This cumbersome and uncomfortable, 15-20 minute process performed by an engineer with a quasi-magnetic network analyzer will alone preclude the use of this coil and method for any but the most desperate, experienced, and equipped experimentalists. The transmit-receive (T/R) switches and preamps for this transceiver coil are at the end of lossy coax cables, remote from the coil. Incorporation of additional advantageous features like nested receiver arrays or multi-nuclear elements are not a possibility with this basic coil. Further, the coil being made of copper-foil elements and shield material wrapped around a rigid 2.5-cm thick×17.3 cm×41.3 cm Teflon® block is uncomfortably heavy and non conforming to the anatomy. Electrically, it is open with exposed conductors. The Teflon® is thermally unstable, and shifts the frequency of the elements as the coil warms up during pulsing, and with body heat. Mechanically the coil is unstable as well. This coil has served its purpose (feasibility demonstration) but needs to be retired.

Figure 2B:
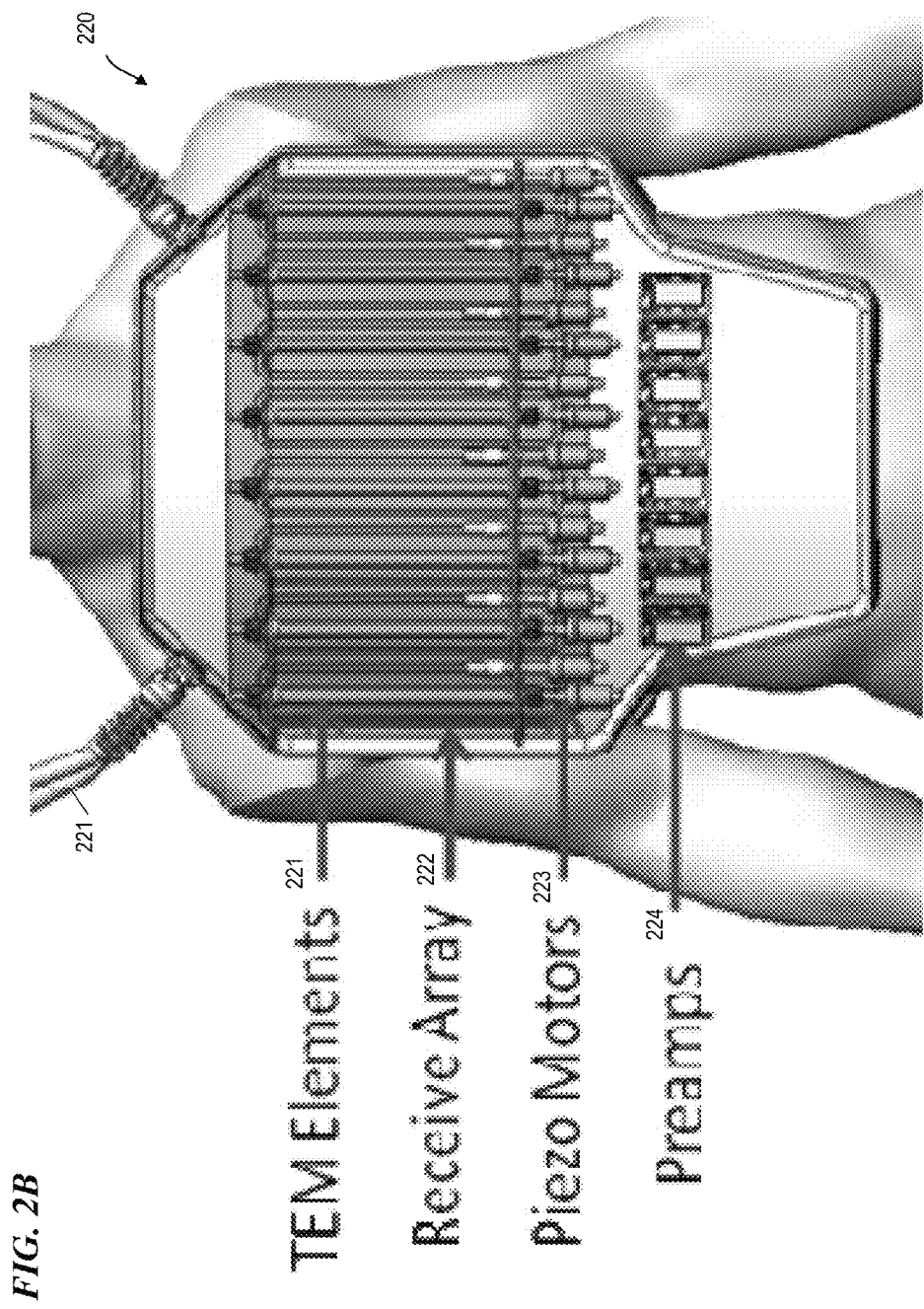
FIG. 2B is a diagram of an auto-tuned cardiac coil 220 of one embodiment of the present invention.

Our invention replaces prototype feasibility coils of FIG. 2A with research-grade utility coils FIG. 2B by incorporating a host of new innovations, the sum of which will render the 7-T MR system a powerful instrument for human cardiac imaging and spectroscopy. This invention includes developing the coil form factor in FIG. 2b in five, progressively innovative, steps:

A.) The first coil will use the form of FIG. 2B, but will be lighter, more electrically efficient and thermally stable with air as the dielectric between the element and the slotted shield. T/R switches and preamps will be onboard the coil, eliminating cable losses before the first amplification stage. Innovative new shield capacitance decoupling will replace bridge capacitor decoupling between the TEM elements, to limit loss and preserve field (reference 14; Vaughan, 2009 #320). (14)

B.) The second coil will incorporate, for the first time, a critical necessity: auto-tuning capability. At lower 1.5-T and 3-T fields, precise tuning and matching of large, monolithic resonators is less critical. RF field penetration, uniformity, and coil efficiency are better; miss-matched loads are more tolerable. Therefore, fixed tuned and matched transmitters are the standard. At 300 MHz however, large, single transmit coils are replaced by parallel arrays of small resonant elements, and they must be tuned and matched to a proportionately lossier load. The only conceivable coil for practical 7-T cardiac imaging must have 16 or more actively tuned, matched, and electromagnetically (EM) shimmed elements. Therefore the 16-channel auto-tuned transceiver is the second coil to be completed and evaluated.

C.) The third coil adds a separate 32-channel receive array, nested symmetrically inside the 16-channel TEM transmit array of A.) and B.) above. This design extends auto tuning and matching to a multi-channel transmit coil with a 32-channel receiver for improved signal detection and parallel imaging performance.

D.) The fourth coil brings human cardiac spectroscopy for the first time to 7T. The design basis of this coil began with B.) above, but alternates the tuning of even and odd TEM elements between 300 MHz for $^1$H NMR (proton nuclear magnetic resonance), and 120 MHz for $^{31}$P MRS (phosphorus magnetic resonance spectroscopy).

E.) The fifth and final coil tunes even and odd transmit elements in coil of C.), to 300 MHz and 120 MHz respectively. Similarly, symmetrically distributed receiver elements are tuned alternately to the proton and phosphorous frequencies. This coil has the highest performance for proton scout imaging and shimming, with efficient and uniform excitation and detection on of $^{31}$P spectra.

FIG. 2A is a photograph of a conventional cardiac coil 219. One half of a pair of eight-channel TEM arrays (eight copper coil elements mounted on a dielectric substrate, and connected to eight respective cables) and is shown. This is the coil was used to demonstrate the feasibility of 7-T cardiac imaging.

FIG. 2B is a diagram of a cardiac coil 220 of one embodiment of the present invention, with one half of a pair of eight-channel TEM arrays nested with receive arrays is shown. In some embodiments, eight TEM elements 221, each having ONE piezo motor 223 for tuning, AND ONE piezo motor 223 FOR MATCHING, and an array of eight receive elements 222 each connected to its own onboard preamplifier 224. This coil also incorporates auto-tuning capability.

Electromagnetic (EM) Shimming

The electromagnetic (EM) fields that RF coils generate can be separated into the electric (E) and magnetic (B) fields. The net E-field interacts with the tissues and is responsible for RF heating, expressed as the Specific Absorption Ratio (SAR). Due to the spin of the nucleus, the B-field is further broken down into two oppositely rotating components: $B_1^+$, which corresponds to the transmitting field, and $B_1^-$, which represents the reception field of an RF coil. It has been shown that the phase and/or magnitude of individual coils can be modified to improve the constructive interference of the $B_1^+$ fields over an ROI ($B_1^+$ shimming). This can reduce the SAR by improving the efficiency (flip angle versus input power) of the array.(11, 15, 16) Improving $B_1^+$ shimming will continue to be an active area of research, but it will be expanded to include an estimated E-field and resulting SAR. By optimizing the magnetic field and minimizing the electric field interactions in the body, or EM shimming, we hope to further reduce SAR limitations during RF intensive pulse sequences.

While the $B_1^+$ field can be measured directly with MR, the electric field cannot be practically measured—it can only be simulated. Finite difference time domain (FDTD) electromagnetic (EM) simulations require substantial computational time (days). Therefore, we describe a hybrid technique to incorporate SAR estimations into the optimization criteria. The $B_1^+$ fields are calculated from data acquired from the patient in the magnet (e.g., a phase map of image data from a known excitation), but the resulting SAR from a particular $B_1^+$ shim configuration will be estimated from the linear superposition of the previously calculated E-fields of an FDTD model of the RF array on a full-human model. Of course, the SAR is a prediction from the model, but this is a valid estimation for several reasons. First, multiple body shapes will be modeled with FDTD beforehand. A catalogued modeled library will be composed and will allow us to choose an EM model that most closely resembles the patient. Secondly, even at 7 T, it has been shown that the SAR distribution is substantially similar across several different body models.(17) Thirdly, it is expected the highest, and therefore most restrictive, SAR will occur in the intercostal tissue near elements, which dramatically reduces the importance of matching the dimensions of the width or thickness of an individual to a particular model. FIGS. 3*b* and 3*d* are examples of the SAR concentrated in the periphery. At first, the SAR estimation will be calculated, but it will not influence the $B_1^+$ shim. After the algorithm is refined and stable, the SAR estimation will be used as a penalty parameter during shim optimization calculations. This will require appropriate weighting of two criteria, homogeneous $B_1^+$ and minimum local SAR, in calculating the optimal EM shim.

Figure 3:
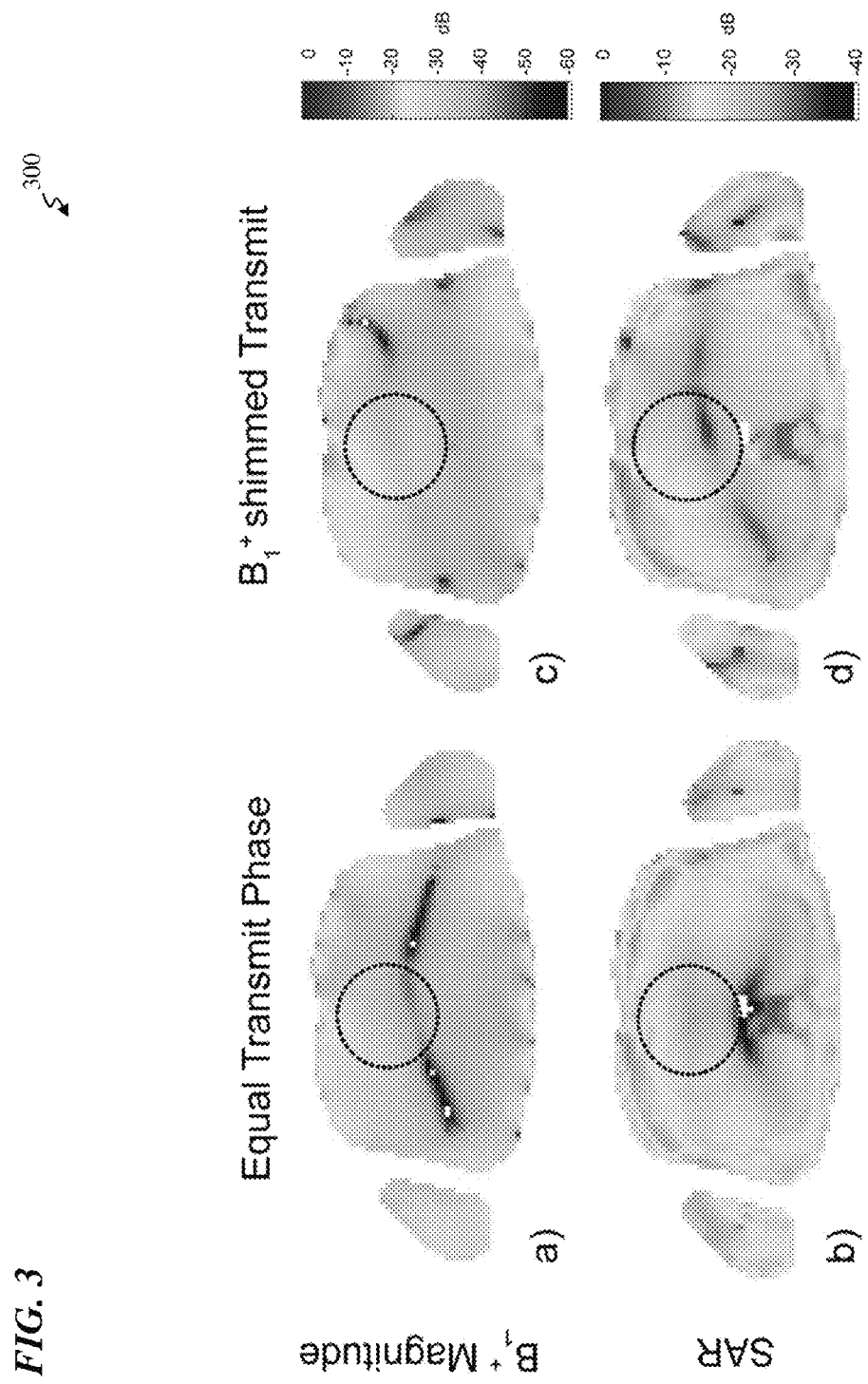
FIG. 3 shows FDTD simulations of the 16-channel RF array in two shimming configurations: (a) and (c) are thorax cross-sectional graphs of calculated $B_1$ field magnitudes, while (b) and (d) are calculated SAR magnitudes. In the cross-sectional thorax simulation graph (a), the $B_1$-field magnitudes to all the transmit elements are being transmitted with equal phases to all elements; however, when going to the simulation graph (c) we reset ("shim") the phase angles at each element in order to obtain improved (higher) $B_1$ field magnitude and better uniformity by adjusting phase angles of the $B_1$ transmit signal to each coil element to image the heart; (b) (unshimmed) to (d) (shimmed) shows considerably lower SAR magnitudes in parts of the heart region.

FIG. 3 shows FDTD simulations of the 16-channel RF array in two shimming configurations. The phase of each coil is the same in figs a) and b), but shimmed over the heart (indicated by the circle) in figs c) and d). In the posterior of the heart, the efficiency has been improved without significant increase in SAR.

Capacitive Shield Decoupling

Figure 4A:
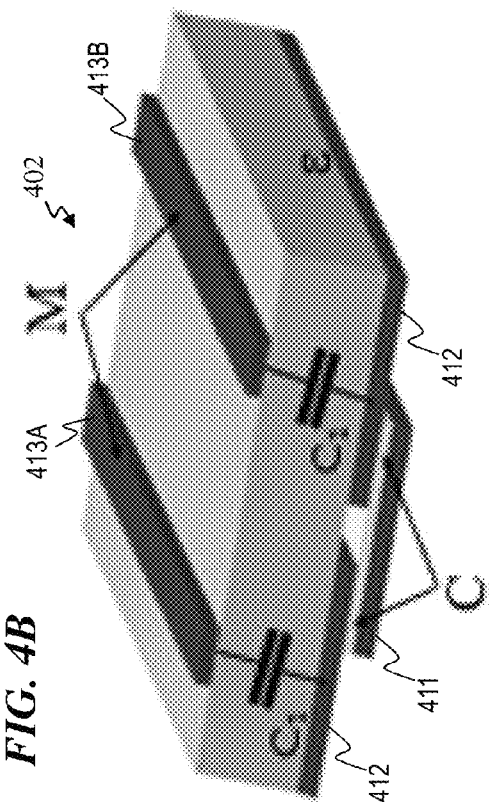
FIG. 4A shows a perspective schematic view of two transmit elements 413A and 413B of a conventional birdcage coil 401.
Figure 4B:
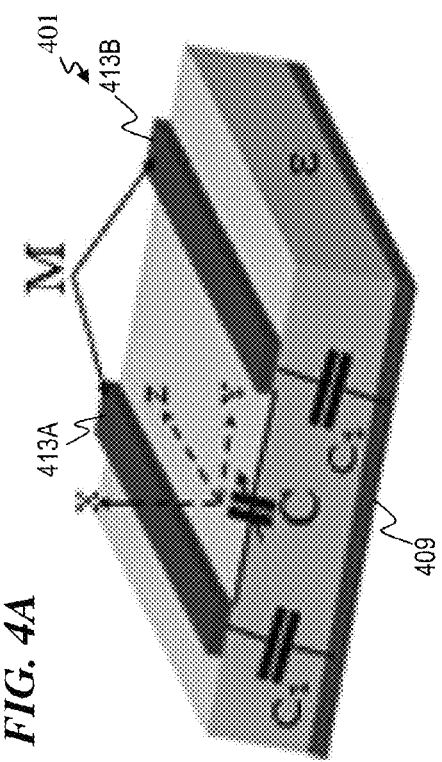
FIG. 4B shows a perspective schematic view of two transmit elements 413A and 413B of a conventional TEM coil 402.

To preserve independent control over neighboring transmit elements, and independent $B_1$ field components generated by them, they must be inductively mutually decoupled. The standard approach to decoupling elements is to add a capacitive bridge "C" to balance the mutual inductance "M" shown in FIG. 4A. This method, however, decreases field uniformity by generating secondary circuit loops, as shown in FIG. 4A. The decoupling capacitor, C, can store resonant energy and therefore decreases the overall efficiency of the coil. FIG. 4B shows a new innovation using capacitance in the overlapping layers of our split-shield design to cancel mutual inductance while preserving both energy and field uniformity in the coil. This new decoupling method will be implemented for the first time in the cardiac coils planned for this invention. Decoupling performance is measured by creating a decoupling matrix showing the percent coupling of any element to any other element in the sixteen-element array for the cardiac coils planned.

FIG. 4A shows a perspective schematic view of two transmit elements 413A and 413B of a conventional birdcage coil 401. Transmit element 413A and transmit element 413A are each capacitively coupled to a common shield 409, and their mutual inductance M is compensated by a variable capacitor between them FIG. 4B shows a perspective schematic view of two transmit elements 413A and 413B of a conventional TEM coil 402. In this conventional embodiment, transmit element 413A and transmit element 413A are each capacitively coupled to their own separate shields 412 that are separated from one another by a small lengthwise gap, and each of these are covered by separated outer shields 411. Each transmit element can be separately driven.

Figure 4C:
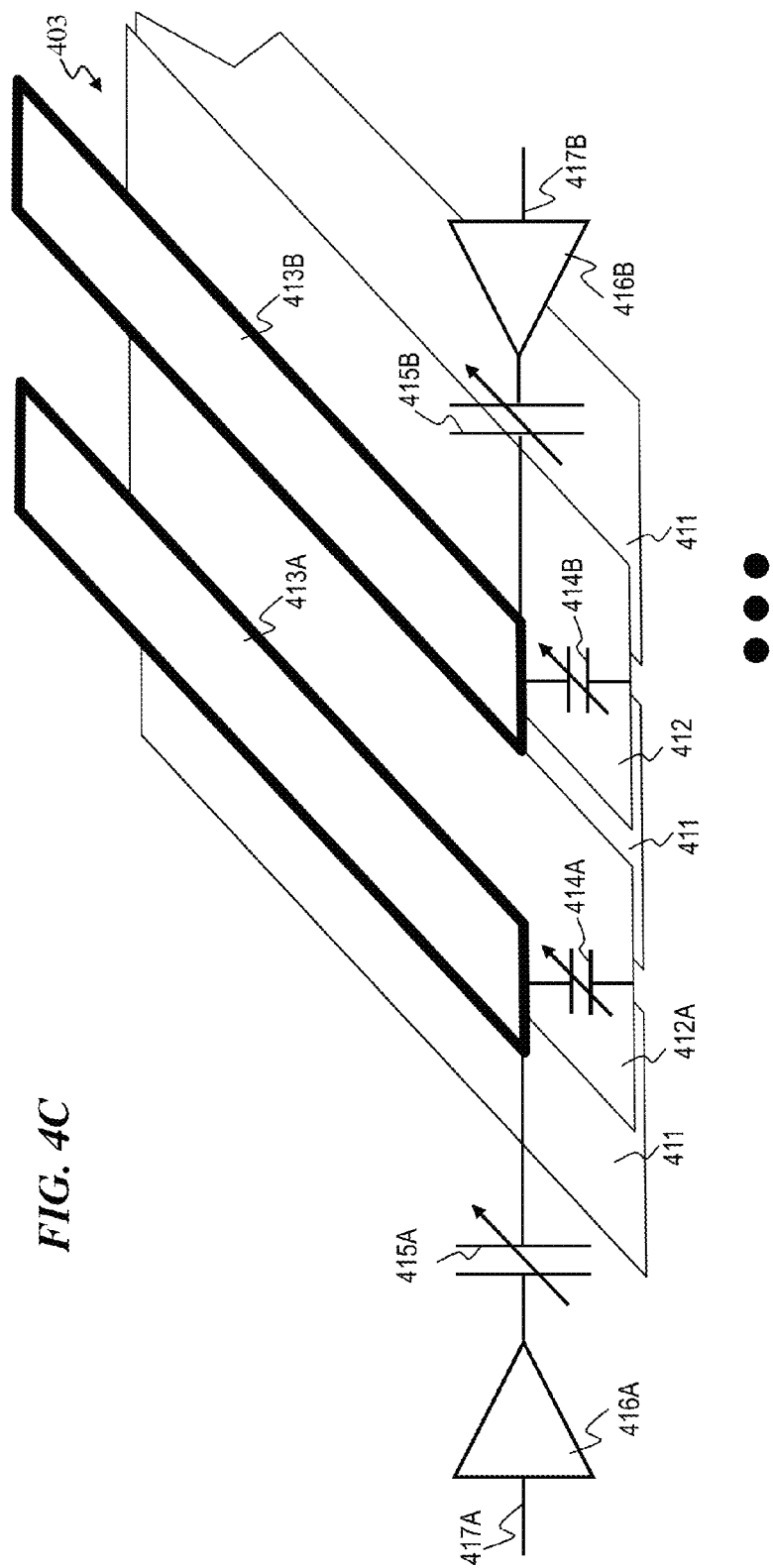
FIG. 4C shows a perspective schematic view of two transmit elements 413A and 413B of auto-adjusted TEM coil 403 according to some embodiments of the present invention.

FIG. 4C shows a perspective schematic view of two transmit elements 413A and 413B of auto-adjusted TEM coil 403 according to some embodiments of the present invention. The improvement provided by the present invention is that each transmit element can be automatically individually frequency tuned (e.g., by a series-connected non-magnetic variable capacitance 415 connected between the respective transmit amplifier 416 and the transmit element 413) and individually impedance matched (e.g., by a parallel-connected non-magnetic variable capacitance 414 connected between the respective shield 412 and the transmit element 413). This FIG. 4C shows just a small portion of two transmit elements 413A and 413B, their inner shields 412A and 412B, the overlapping outer shields 411, the parallel-connected variable impedance-matching capacitors 414A and 414B, the series-connected variable resonance-frequency-tuning capacitors 415A and 415B, the power amplifiers 416A and 416B of the transmit circuit (in some embodiments, these power amplifiers are non-magnetic class-D power amplifiers located in the coil unit), and the transmit signal wires or fibers 417A and 417B. In various embodiments, the coil units of the present invention use 16 or 32 transmit elements and 16, 32 or 64 receive channels, however any suitable number of transmit elements and receive channels may be used—the invention is not limited by the number used. FIG. 4C omits the receive loops for clarity of presentation. See the figures below for exemplary receive configurations.

Figure 4D:
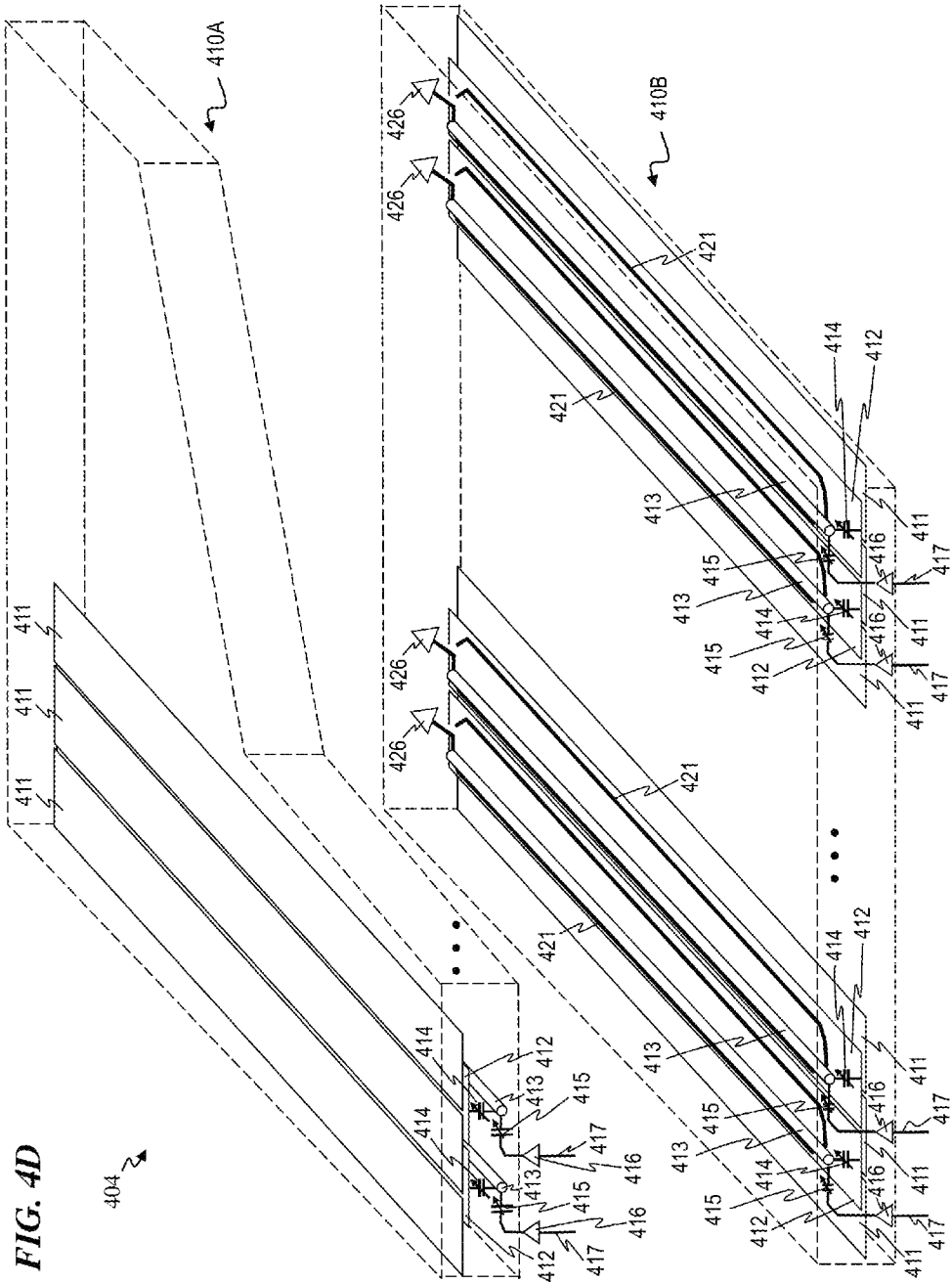
FIG. 4D shows a perspective schematic view of two auto-adjusted TEM coils 410A and 410B according to some embodiments of the present invention.
Figures 8A, 8B:
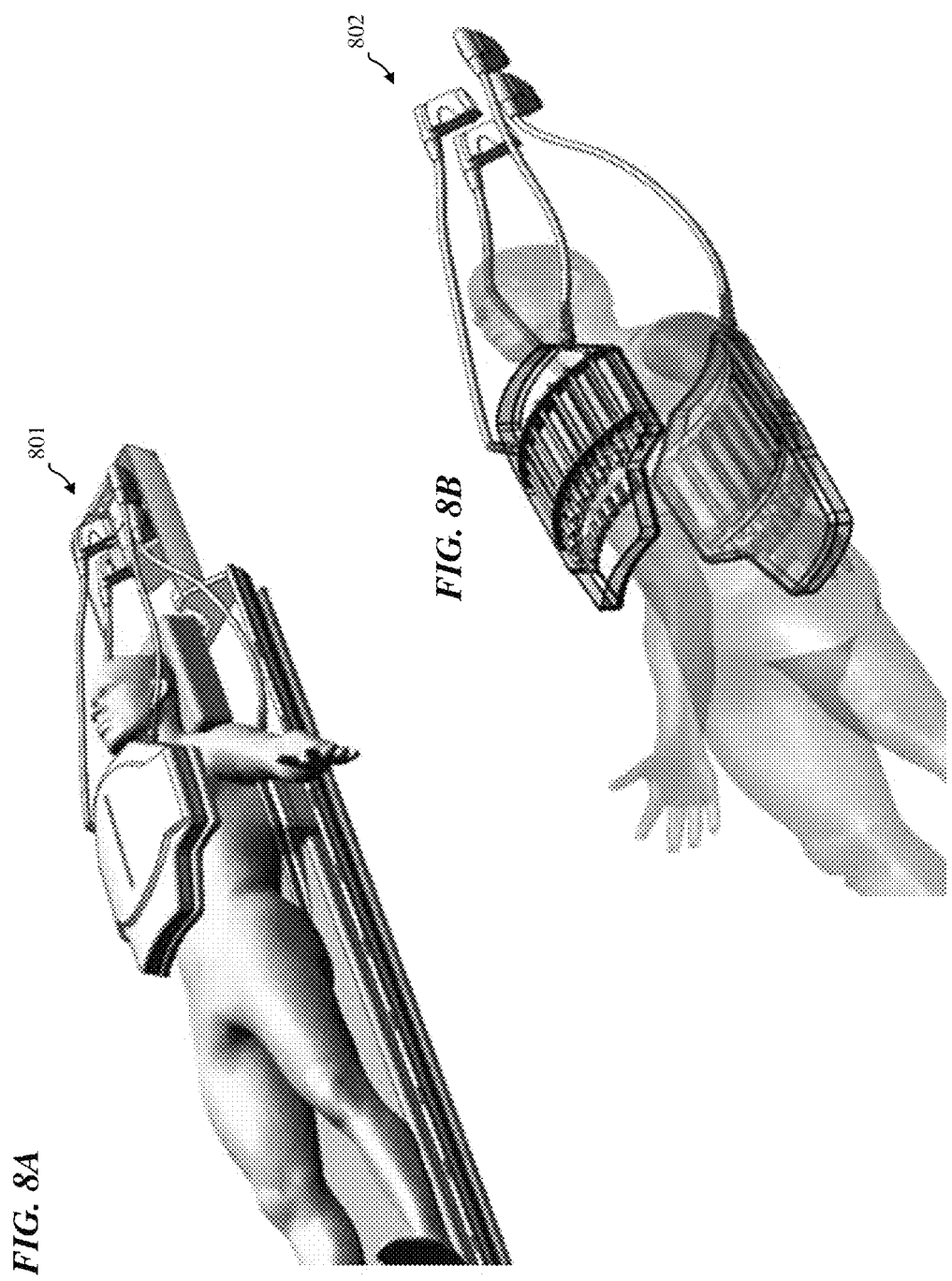
FIG. 8B show a partially transparent view that shows a plurality of TEM elements above and below the body.

FIG. 4D shows a perspective schematic view of a cardiac-imaging coils system 404 having two auto-adjusted TEM coils 410A and 410B according to some embodiments of the present invention. In some embodiments, each of the TEM coils 410A and 410B includes a plurality of transmit units each including a transmit element 413 (e.g., a rod, rectangular prism or other suitable shape (e.g., in some embodiments, a copper trace on a flexible circuit board), an inner shield 412, the overlapping outer shields 411, the parallel-connected variable impedance-matching capacitor 414, the series-connected variable resonance-frequency-tuning capacitor 415, power amplifier 416 of the transmit circuit, and transmit signal wire or fiber 417. Also shown is a plurality of receive loops 421 each connected to its respective preamplifier 426. In some embodiments, all of the components shown are assembled into the unit 801 shown in FIG. 8A. In other embodiments, all of the components shown except for the transmit amplifiers 416 are assembled into the unit 801 shown in FIG. 8A, and the transmit amplifiers are located remote from the magnet bore.

FIG. 4E shows a perspective schematic view of a single transmit-receive element 405 according to some embodiments of the present invention. In some embodiments, TEM coils (such as 410A and 410B of FIG. 4D or coils 801 of FIG. 8A) each include a plurality of such transmit-receive units 405 each including a transmit element 413 (e.g., a rod, rectangular prism or other suitable shape (e.g., in some embodiments, a copper trace on a flexible circuit board), an inner shield 412, the overlapping outer shields 411, the parallel-connected variable impedance-matching capacitor 414, the series-connected variable resonance-frequency-tuning capacitor 415, power amplifier 416, and transmit signal wire or fiber 417. Also included is a receive loop 421 connected to a differential preamplifier 426.

FIG. 4F shows a perspective schematic view of a transmit-receive element 406 according to some embodiments of the present invention. In some embodiments, transmit-receive element 406 is substantially similar to transmit-receive element 405 described above, but here are included two receive loops 421A and 421B each connected to a respective differential preamplifier 426A and 426B.

Figure 4G:
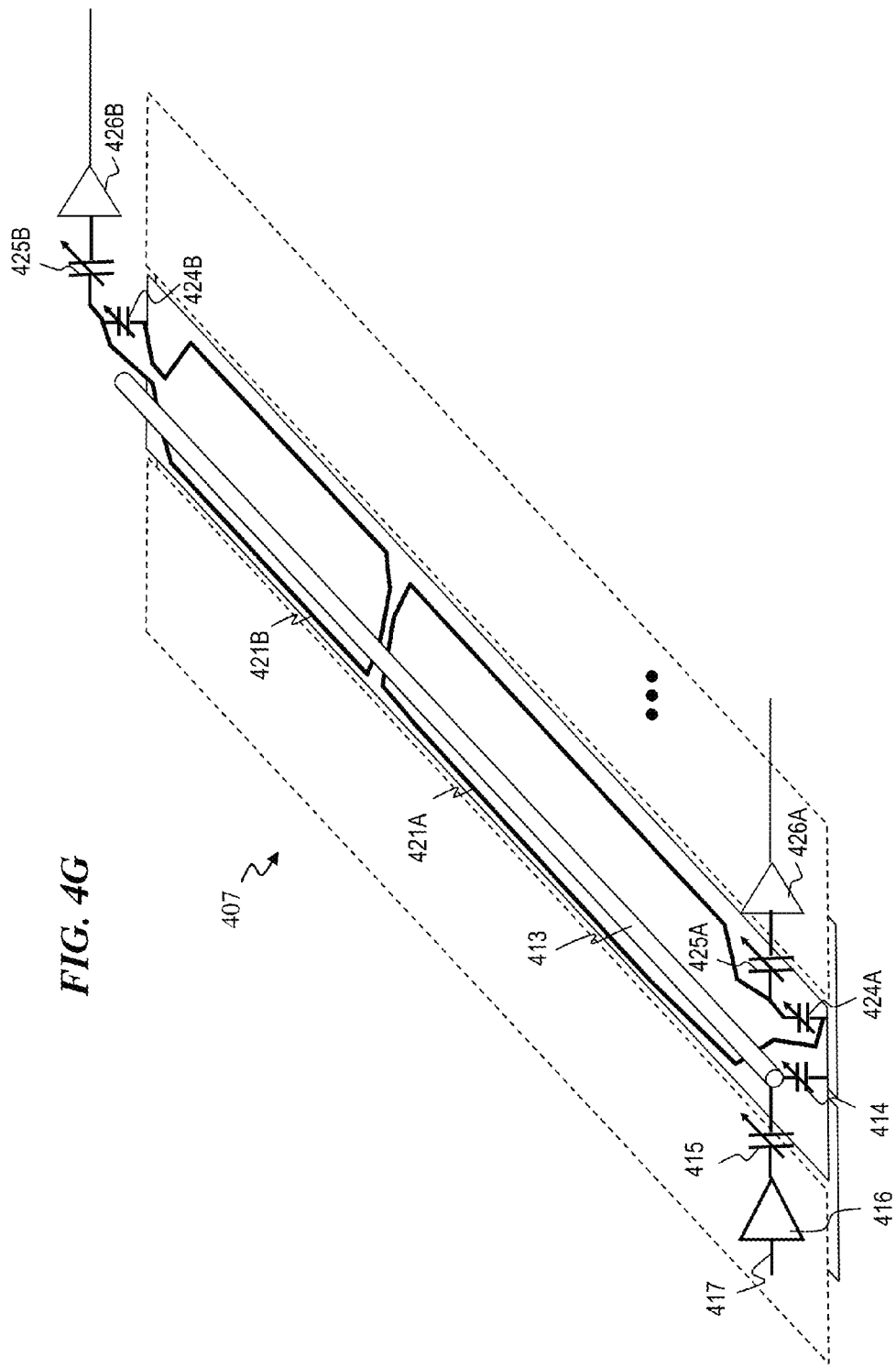
FIG. 4G shows a perspective schematic view of a transmit-receive element 407 according to some embodiments of the present invention.

FIG. 4G shows a perspective schematic view of a transmit-receive element 407 according to some embodiments of the present invention. In some embodiments, transmit-receive element 407 is substantially similar to transmit-receive element 406 described above, but here the two receive loops 421A and 421B are each connected to be impedance matched and resonance frequency matched (e.g., in some embodiments, using parallel-connected variable capacitor 424A to impedance match receive-loop antenna 421A to preamplifier 426A, and series-connected variable capacitor 425A to resonance-frequency match receive-loop antenna 421A to preamplifier 426A, and using parallel-connected variable capacitor 424B to impedance match receive-loop antenna 421B to preamplifier 426B, and series-connected variable capacitor 425B to resonance-frequency match receive-loop antenna 421B to preamplifier 426B). In the embodiment shown there is a two-to-one ratio of receive elements to transmit elements. In other embodiments, a one-to-one ratio is used, (while in yet other embodiments, other ratios of transmit elements to receive elements are used) and impedance and frequency matching are used on both transmit and receive circuits as is shown and described here.

Figure 4H:
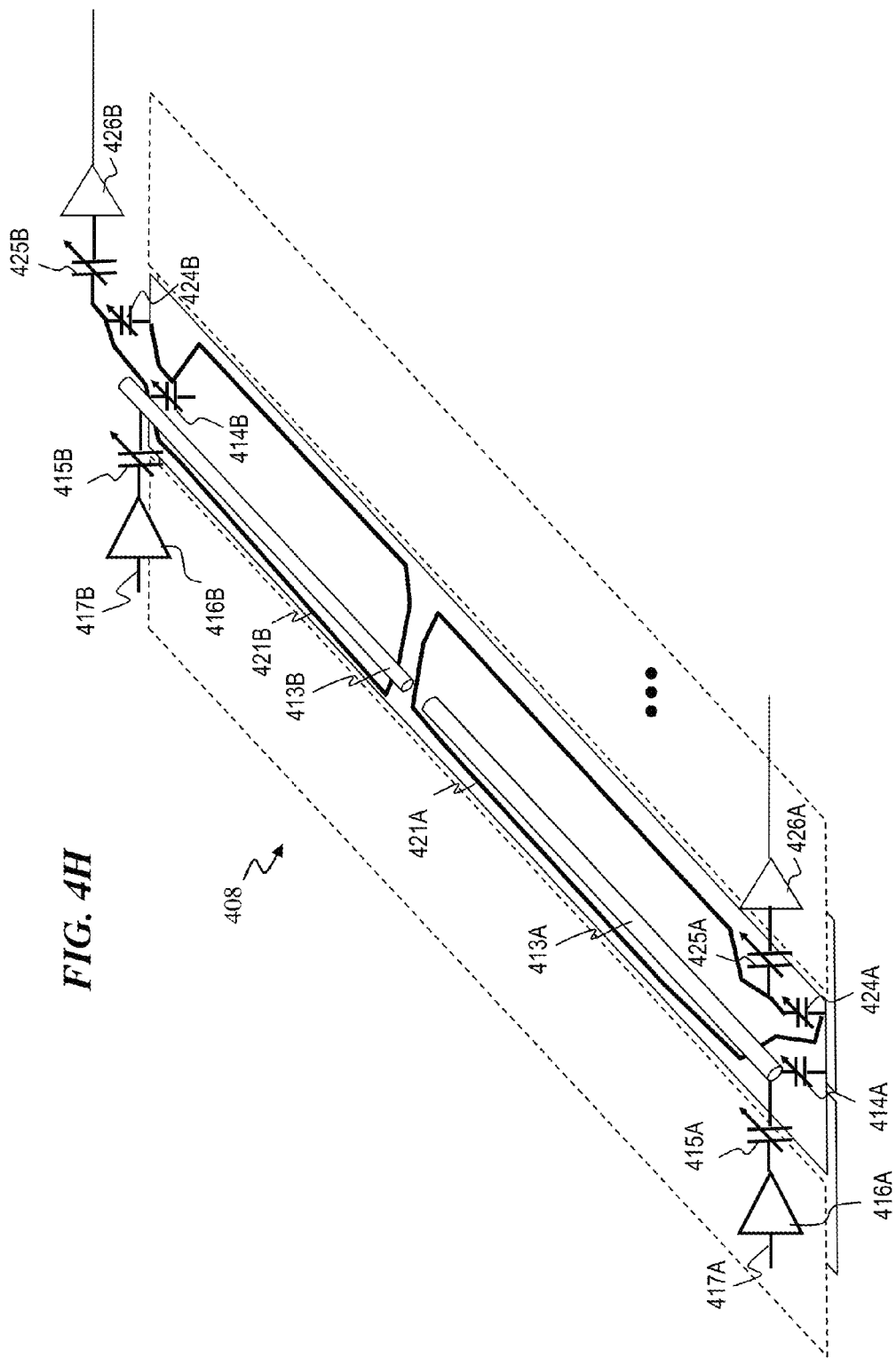
FIG. 4H shows a perspective schematic view of a transmit-receive element 408 according to some embodiments of the present invention.

FIG. 4H shows a perspective schematic view of a transmit-receive element 408 according to some embodiments of the present invention. As just described, a one-to-one ratio of receive elements to transmit elements is used, with two rows of transmit elements 413A and 413B being used with two rows of receive loops 421A and 421B. A plurality of such elements 408 are implemented in the top coil unit 410A and a plurality of such elements 408 are implemented in the top coil unit 410B as indicated in FIG. 4D and shown in the system of FIG. 8A.

Piezo Motor Tuning and Matching

Figure 5:
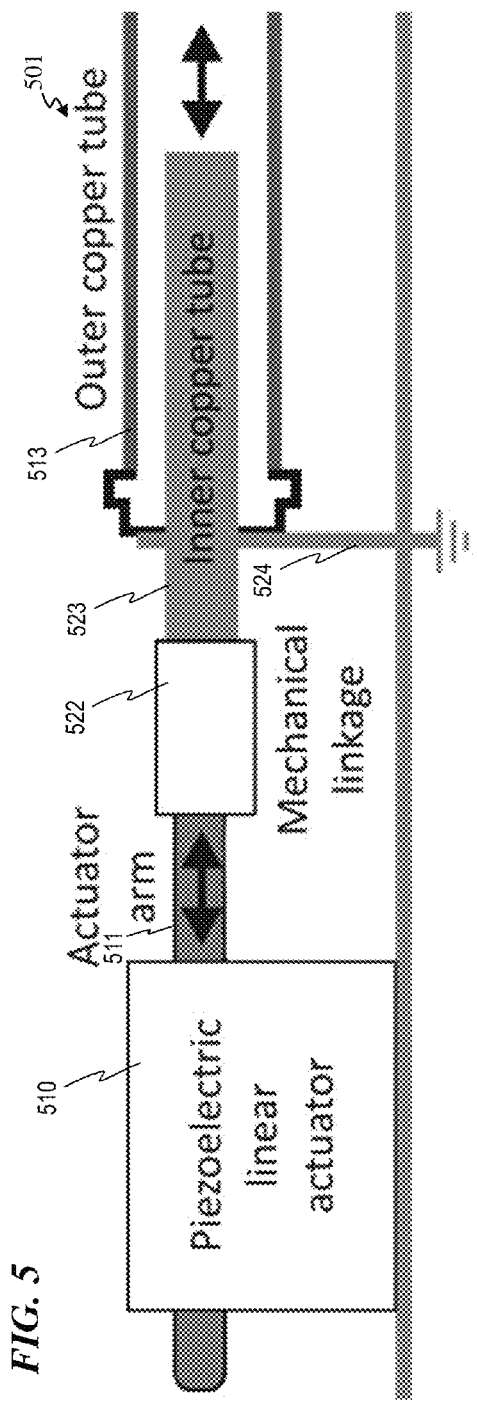
FIG. 5 shows a piezo motor 510 used to capacitively tune and impedance match a "coil-element" circuit 501.

FIG. 5 shows a piezo motor used to capacitively tune and match a "coil" circuit. There will be a tune and match pair of these circuits for each of 16 coil elements.

The quality factor, or Q, of the ultra-high-frequency TEM elements is relatively high, which means that the 3-dB bandwidth of the element's resonance is relatively narrow. Since the resonance frequency is load dependent, the coil elements must be adjusted for each subject to minimize losses during transmission and/or reception. Without automatic tuning and impedance matching of the multiple coil elements, the scientific and clinical utility of these multi-channel transmit methods will not be realized. Previous efforts in remote tuning have been restricted to low-power coils because the active components would fail at transmit power levels.(18, 19) Therefore, the development of the means to automatically tune and match every transmit coil as specified in the Embodiments is an important innovation. To develop autotune capability, a non-magnetic, linear piezoelectric-actuated reactance (capacitance or inductance) for controlling tuning and matching operations per element will be incorporated in the coils. Initially, the piezoelectric motor will move the center conductor in a coaxial TEM coil element to efficiently and smoothly adjust the impedance of the element. The whole tuning and matching process will be algorithm-driven from the console.

Multi-Nuclear Spectroscopy

Figure 6:
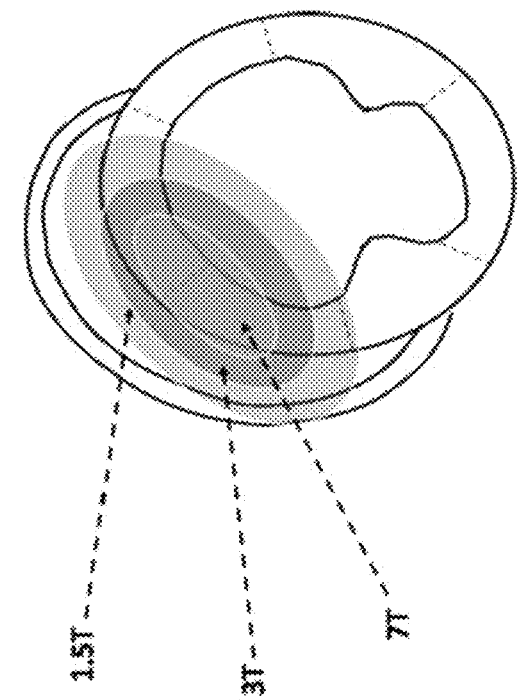
FIG. 6 shows relative voxel sizes comparison of 1.5 T, 3 T, and 7 T for a given NMR signal. (7T-4 cc voxel for $^{31}$P for high-energy phosphate metabolism analysis) {Hudsmith, 2009 #341}
Figure 7A:
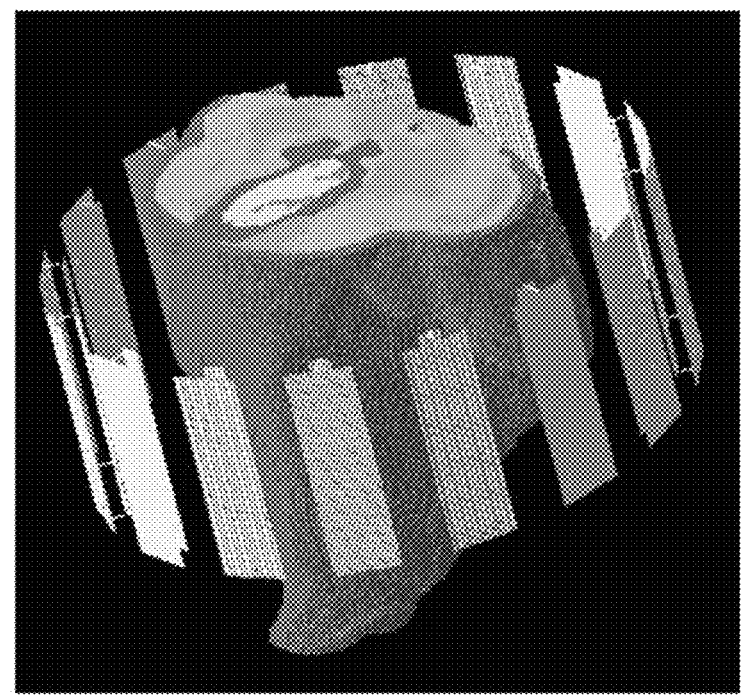
FIG. 7A shows general configuration of the porcine head.
Figure 7B:
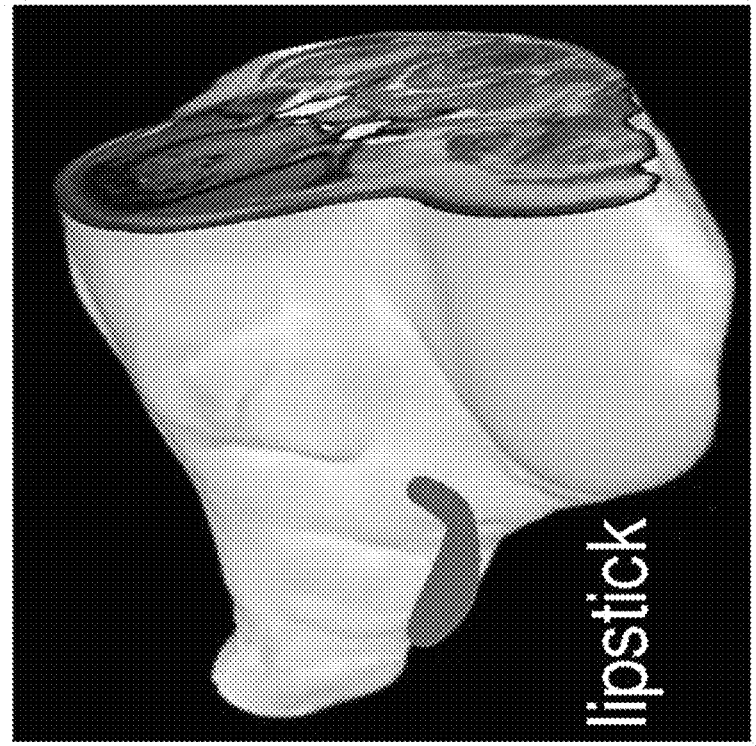
FIG. 7B shows the porcine head surrounded by coil elements.
Figure 7D:
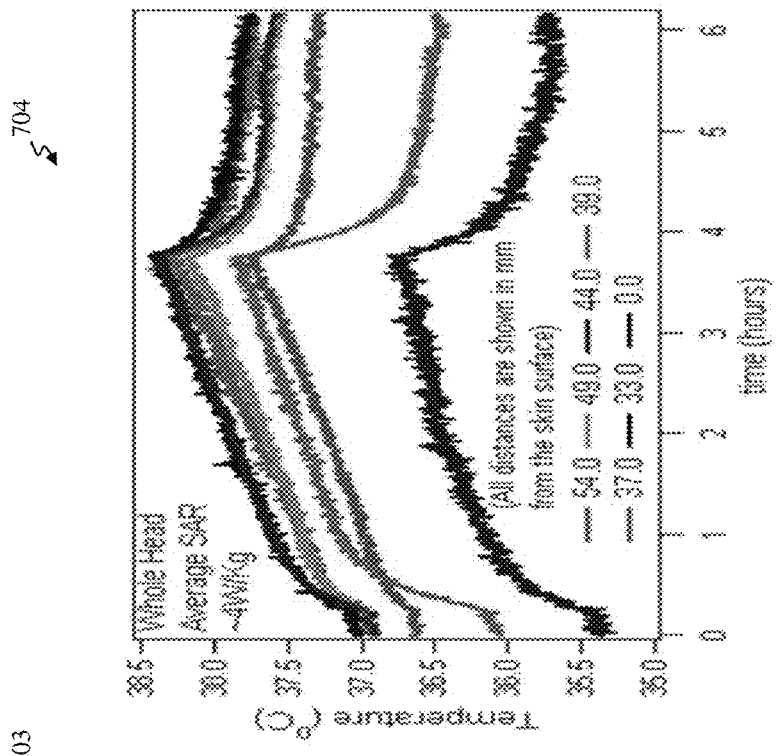
FIG. 7D shows temperature sensor parameters measured at different distances from the skin surface.
Figure 7C:
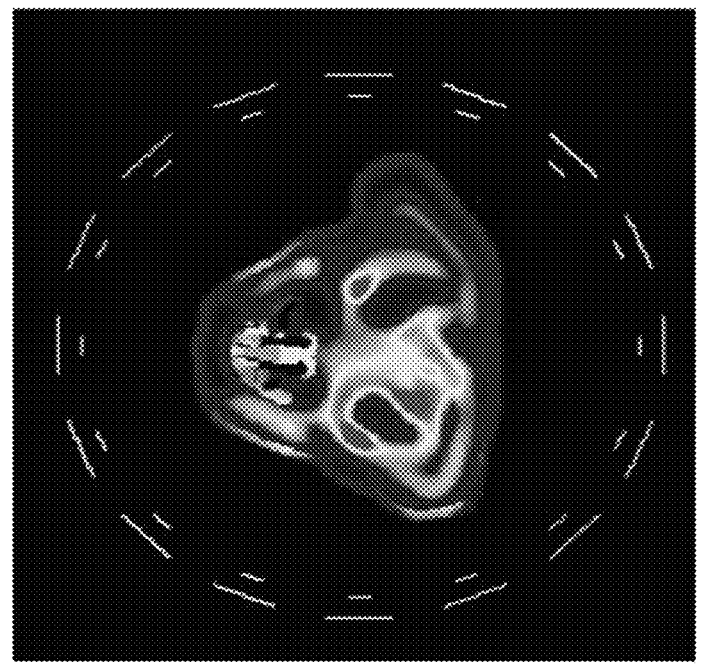
FIG. 7C shows a Specific Absorption Rates (SAR) map of a porcine head surrounded by TEM elements.

FIG. 6 shows voxel-size comparison of 1.5 T, 3 T, and 7 T for a given NMR signal. {Hudsmith, 2009 #341} For the first time, 7 T brings the SNR and spectral resolution for $^{31}$P spectroscopy required for signal acquisition from heart-wall-sized voxels (down to 2 cc). {Cho, 2001 #299} This opens many possibilities for metabolic observation of infarct regions, allografs, and other conditions without partial volume contamination from intercostal muscle and the blood pool. The multi-nuclear coils planned will make possible the first spectroscopic investigations of the whole heart in humans at 7 T.

Thermal Modeling and Measurement

New coil development cannot proceed without a parallel investigation determining the safety of new coils in the context of their applications. While the industry too much relies on SAR calculations from cartoons of anatomy, this is not sufficient for determining RF safety. Our institutional review board (IRB) and Food and Drug Administration (FDA) investigational-device exemptions subscribe to our using temperature as determined from the World Health Organization recommended porcine heating model as the most accurate method for thermal safety determination. SAR is but one of six variables in the well-known Pennes Bio-heat equation, and one of seven in the more-general and also now well-known Shrivastava-Vaughan equation, which also accounts for blood temperature. SAR by itself, ignoring the thermodynamics and thermoregulatory reflexes of a living system, is a poor predictor of temperature. Therefore, our laboratory not only calculates SAR and temperature contours, but validates these model predictions with direct temperature measurements. Because the direct measurements are invasive, they cannot be performed on humans. By directly measuring the temperature in live pig tissue by fluoroptic thermometry, we can correlate temperature to SAR measurements, which in turn are monitored by the MR system. For each new coil and pulse sequence, we correlate and calibrate system SAR measurements to actual temperature measurements, and set SAR thresholds accordingly to the FDA Guideline, or to our thermally identified guideline, whichever is the most conservative (most safe). Our approach we feel is safer and more informed than that of industry SAR monitoring or FDA Guidelines alone, and a true innovation above current standards. Porcine head models and measurements are shown in FIG. 7. An anatomic atlas and pig body model must be constructed for the project, another innovation planned. In summary, we predict, monitor and adhere to FDA, SAR guidelines. We add to this an extra measure of safety by predicting and measuring temperature as well. Our temperature work sets us apart from convention, is a more informed and safer direction.

FIG. 7. a.) shows the pig head imaged for creating a digital anatomy atlas. With this atlas, we can predict b.) the $B_1$ field in the coil and head, c.), the SAR in the head, and temperature contours not shown. By correlating system-monitored SAR to direct temperature measurements from the anatomy d.) we can better assure that our new coils and experiments using them are safe.

In some embodiments, the invention is based on five coils of increasing complexity and innovation. The coils represent a progressive design series, with each coil extending to the next, one innovation at a time. The basis of all five coils is a 16-element TEM array packaged as a pair of eight-element anterior and posterior halves. (See FIG. 8, which shows a sixteen-channel TEM array fully packaged in place on a subject (left), and open with both halves visible (right).) The coil pairs will be housed in ergonomic forms of molded plastic, and connectorized to the Siemens 7-T system with Siemens connectors as shown. This will provide a robust, utility platform for further coil development. As a standard method, each coil in the series will be first designed by finite-difference time-domain modeling (e.g., in some embodiments, XFDTD-brand of XDTD, available from Remcom, Inc. St. College, Pa.) of human-loaded coil circuits, dimensions and materials to obtain the desired maximized $B_1$ field and minimal SAR contour for the human chest as shown in FIG. 3. Once a coil model is shown to generate the design field for an ROI (region of interest), the coil will be constructed, bench tested, safety tested, implemented, and evaluated with image data acquired from volunteer subjects. Details specific to the design, building and testing of each of the coils, follow.

1. 16-Channel Transceiver Coil

The conventional prior-art 16-channel transceiver coil (FIG. 2a) is improved upon by the 16-channel TEM transceiver shown in FIG. 8. The design is derived from extensive modeling; the new coil includes coaxial array elements and is much lighter and more efficient, having air dielectric between the elements and the slotted shield. Per FIG. 4, the new coil includes shield capacitance for the first time to more efficiently decouple the elements without perturbing the field. It also includes on-board T/R switches and pre-amps. To bench test the constructed coil, basic network analyzer measurements S11 measure the capacitive impedance matching and frequency tuning of each element. A receiver probe measuring S12 will determine the field efficiency for a reference input power. Smith chart measurements too will be employed for determination of match and Q, another measure of coil efficiency. If the coil elements are tuned, matched, and more efficient than the previous coil of FIG. 2, with more $B_1$ field detected over the probed field or view within the coil, then we have an improved, higher performance cardiac coil. Our design goal is for a 50% efficiency improvement with this design. The coil must then be tested to be safe. Following the method described in FIG. 7, the coil pair will be fitted to an anesthetized pig instrumented with fluoroptic probes. RF power will be transmitted to the coil pair from the 7-T system power amplifiers at the maximum FDA guideline SAR. If the FDA temperature guideline of 2° C. above core temperature for the trunk is reached, the SAR level and time will be noted, and the RF power turned off. If the experiment continues for two hours without reaching 2° C., the SAR at that point will be noted and the experiment ended. In this way, actual unsafe heating is correlated to easily monitored system SAR. Because a pig is not a human, the SAR threshold will be set at half that required to reach 2° C. in a pig for a given time period, to better assure erring on the safe side. In this way, RF coils and sequences driving them will be safety tested . . . in addition to the SAR model calculations also done. To minimize the number of pigs sacrificed for this experiment, six pigs will be used twice each in vivo for statistically significant 12 studies for each coil.

After a coil a coil is built, bench tested, and safety tested outside of the magnet, it is subjected to a battery of tests on the scanner to further ensure coil performance and patient safety. The first tests are always on a loading phantom. Basic tests on a phantom for noise consistency and independence between receiver channels, individual coil-transmit patterns and efficiency, EPI ghosting intensity, overall transmit efficiency, reflected transmit power, and SNR can usually highlight any problems early in the testing phase.

Finally, the coil is safe for evaluation in the magnet on a human subject. As depicted in FIG. 8, the subject is instructed to recline onto the cushioned posterior half of the coil pre-positioned on the 7-T system's patient bed. After placement and training of vector cardiogram (VCG) leads, the padded top half of the coil is then comfortably secured in position over the subject's chest with a Velcro® strap. The subject is then slowly introduced into the magnet and the VCG signal checked. Siemens' newest-release VCG system and software gives reliable gating on every subject, exceeding 100 to date.

Figure 15:
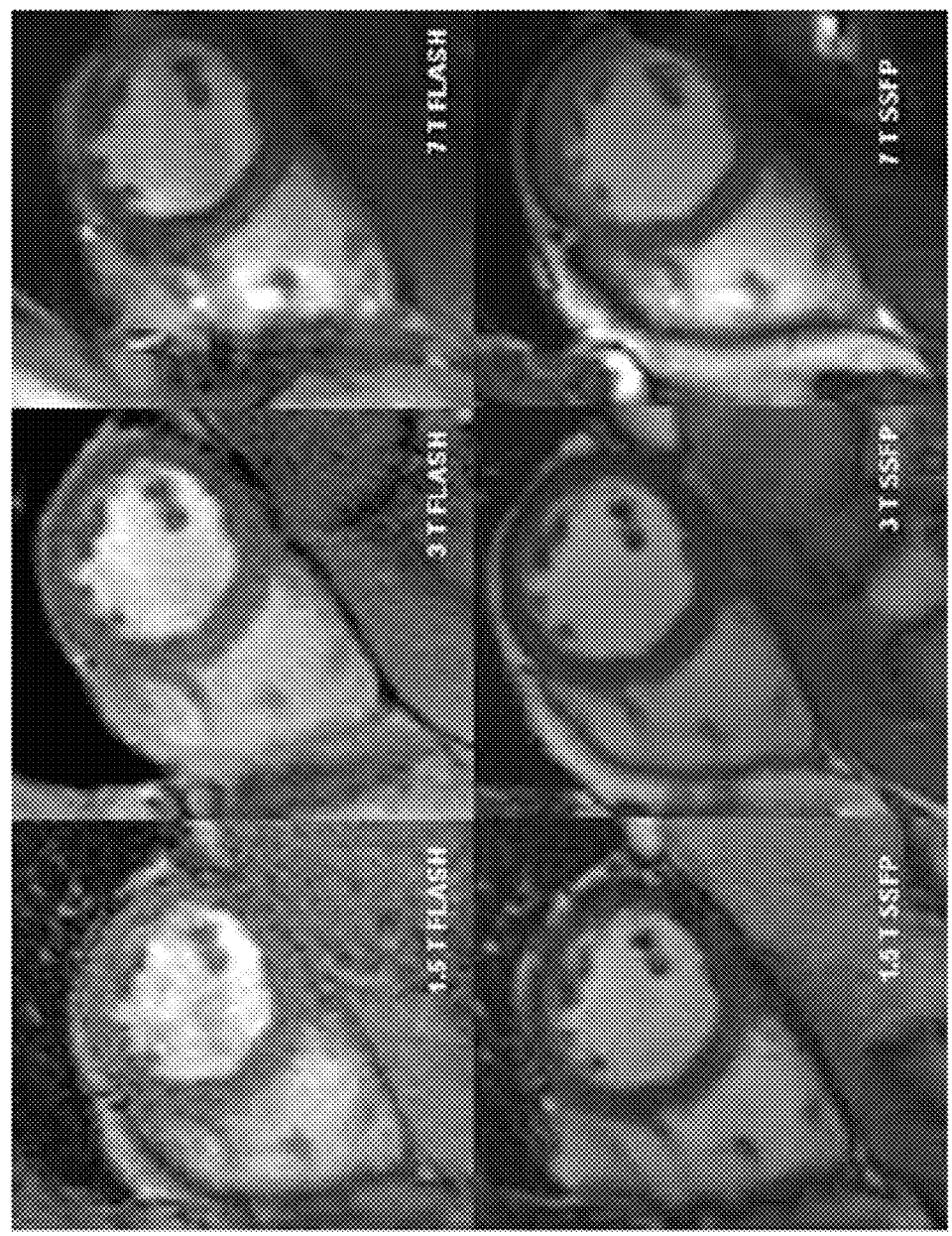
FIG. 15 shows short-axis cine, FLASH and bSSFP, collected on the same volunteer at 1.5 T, 3 T, and 7 T.

First, human measurements will be acquired from the pelvis. The performance of these coils will be more accurately evaluated in a more homogeneous tissue (gluteus maximus), without breathing artifacts and without cardiac motion. Additional criteria such as the array's g-factor, which determines the maximum usable reduction factors in parallel imaging, and overall parallel imaging performance, are examined at this time. The coil efficiency ($B_1^+$) and intrinsic SNR ($B_1^-$) are calculated from two fully relaxed gradient echo images using the double-angle method and specific image-processing methods amenable to SNR analysis. (31,32) {Insko, 1993 #101} {Kellman, 2005 #302} From this information, a transmit-efficiency map in absolute units ($B_1^+$/Volt) is calculated. Similarly, the SNR of the receivers is calculated independent of the transmit field or the console's receive chain. By these metrics comparisons can be made to performance of other coils in our laboratory, and to any reported in the literature. Of course, the real test of a cardiac coil is in cardiac imaging. For clinical insight, three clinical readers (Neubauer, Suttie, Bache) perform a double-blind image quality comparisons made between 1.5-T, 3-T and 7-T cardiac images. Rapid $B_1^+$ maps of the heart will be collected and the relative SNR of the heart will be calculated. (References 34, 35, 36, 37; Cunningham, 2006 #304; Sung, 2008 #400; Sung, 2008 #401.) Refer to FIG. 15 for an example.

2. Auto-Tuned and Matched Transceiver Coil.

In this second Embodiment, the coil of Embodiment 1 will be fitted with piezoelectric actuators and sliding cylindrical capacitors to effect console-driven tuning and matching of the multi-channel transmit array. Of several piezoelectric actuators on the market, we have selected, for some embodiments, the SQ-150NM series from New Scale Technologies (New Scale Technologies, Inc. 121 Victor Heights Parkway, Victor, N.Y. 14564) due to its small package (7.4 mm in diameter and 12.5 mm in length), significant travel distance (50 mm), increased movement resolution (20 nm), high force generation (greater then 5N), and comparatively low cost. While the piezoelectric actuators are not affected by strong magnet fields, most commercial controllers used to drive the piezoelectric devices use iron-core step-up transformers and inductors to generate the voltages necessary to drive the piezo-motor. These controller/drivers fail in strong magnetic fields. Therefore, we design a field-tolerant controller. The controller includes three parts: (1) sine-wave generator, (2) low-pass filter and (3) signal amplifier. Sine-wave generation occurs via two AD9835 direct-digital-synthesis (DDS) ICs (integrated circuits from Analog Devices, One Technology Way, P. O. Box 9106, Norwood, Mass. 02062) synchronized to the same master clock. Low-pass filtering removes phase truncation spurs and Nyquist ghosts associated in the digital-to-analog conversion in the DDS. Finally, control-signal amplification provides the desired drive signals to the piezo motors. Output from the DDS (approximately 0.5 V rms) is amplified, over several stages, to reach the 200 V rms required by the piezoelectric actuators. Apex Precision Power® operational amplifiers by Cirrus Logic, Inc. (2901 Via Fortuna, Austin, Tex. 78746) in conjunction with Communication Power Corporation's (CPC—80 Davids Drive, Suite 3, Hauppauge, N.Y. 11788) 400-V power supply is used for amplification.

Figure 9:
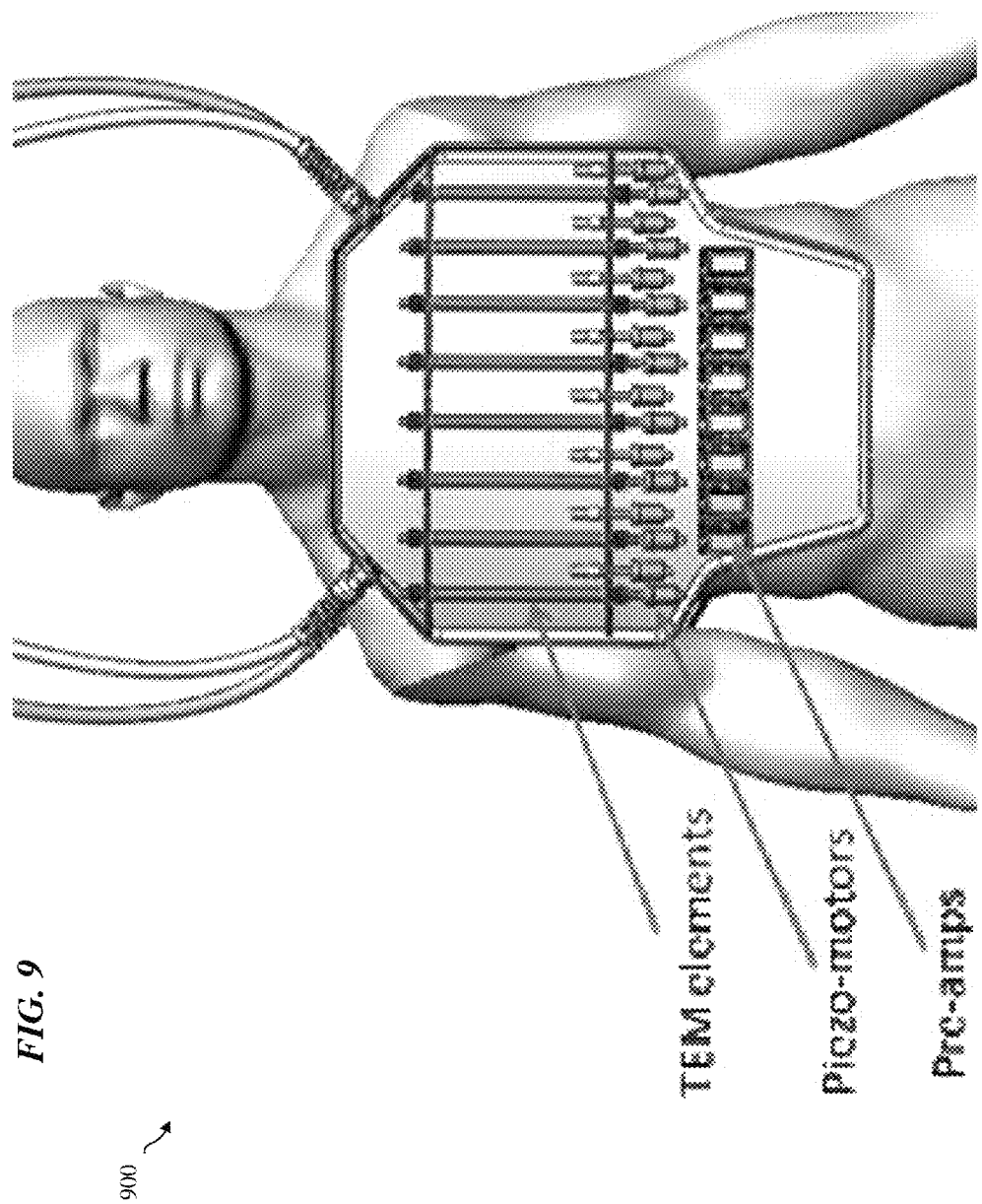
FIG. 9 shows an auto-tuned cardiac coil.

FIG. 9 shows an auto-tuned cardiac coil 900, according to some embodiments.

Auto-Tune Approach

The goal of automated tuning and matching will be achieved by incorporating adjustable capacitors into the coils, which will be driven using non-magnetic, piezoelectric linear actuators. The mechanism of such actuators, which have only recently become commercially available, is non-magnetic and unhindered by the strong $B_0$ magnetic field (reference 8) [8]. FIG. 5 shows a proof-of-concept implementation, where the piezoelectric actuator moves the center conductor in a coaxial TEM coil element, thus efficiently and smoothly adjusting its impedance. Thus, with two actuators the tune and match of a coil element may be adjusted for optimal $B_1$ power.

Figure 10:
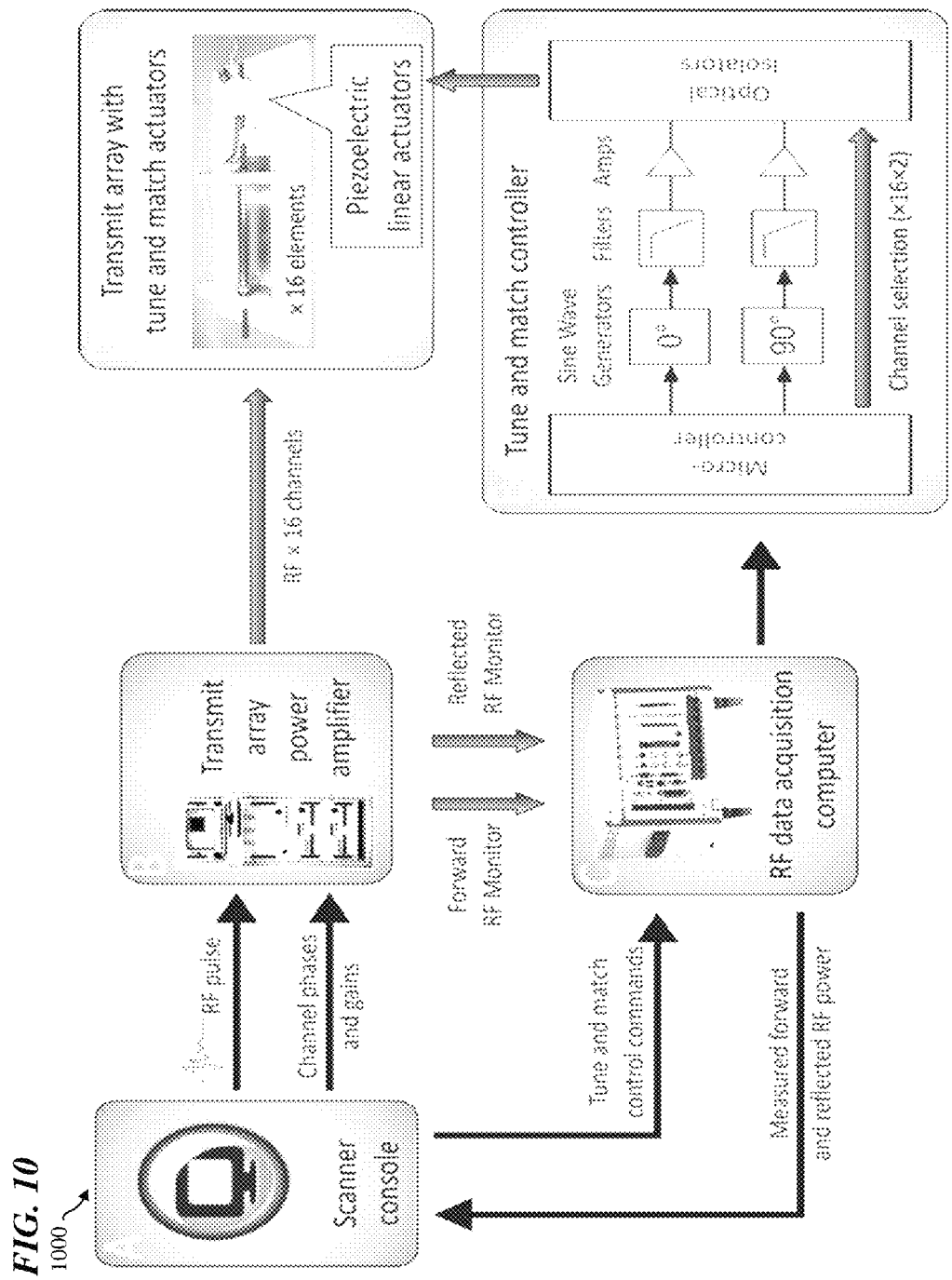
FIG. 10 shows a closed-loop automated system for tuning and matching a cardiac transmit array.

FIG. 10 shows a closed-loop automated system for tuning and matching a cardiac transmit array. A-C are components of the $B_1$-shimming, 7-T MRI system already operating at the University of Minnesota's Center for Magnetic Recording Research (CMRR). D shows a demonstration single TEM element with a piezo motor attached. See FIG. 16 for results. Block E is a microcontroller-based drive unit for the piezoelectric actuators (to be constructed).

The significant advantage of electronic tuning and matching hardware is that it can be controlled by computer, allowing an array coil to be rapidly adjusted without manual intervention. FIG. 10 shows the five key elements to implementing this strategy as applied to our 7-T MRI scanner. Each coil in turn is probed at the Larmor frequency using the scanner's normal $B_1$ shimming RF hardware (A & B), with a "real-time feedback" pulse sequence programmed in the Siemens IDEA environment. The magnitude of the forward and reflected RF power is monitored using pairs of directional couplers built into the RF power amplifiers (B), rectified and digitized with a National Instruments Corporation (11500 N Mopac Expwy, Austin, Tex. 78759) PXI 1042 (C), which is already in use for RF safety monitoring. A computer program running on the console (A) uses these data to decide how to adjust the piezoelectric actuators in each coil (D) and sends appropriate commands to a microcontroller (E) which produces the voltages necessary to move the tune and match actuators. Alterations to the scanner RF output were minimized in order to make this technology easy to transfer to other sites in the future.

Computer control of the tune and match will be effected as follows: Prior to first use, the capacitance is calibrated as a function of steps of the linear actuator. Also, the ratio of forward/reflected power at the Larmor frequency is recorded as a function of the tune and match capacitance, giving "known good" information on the coil Q and matching.

Figure 11:
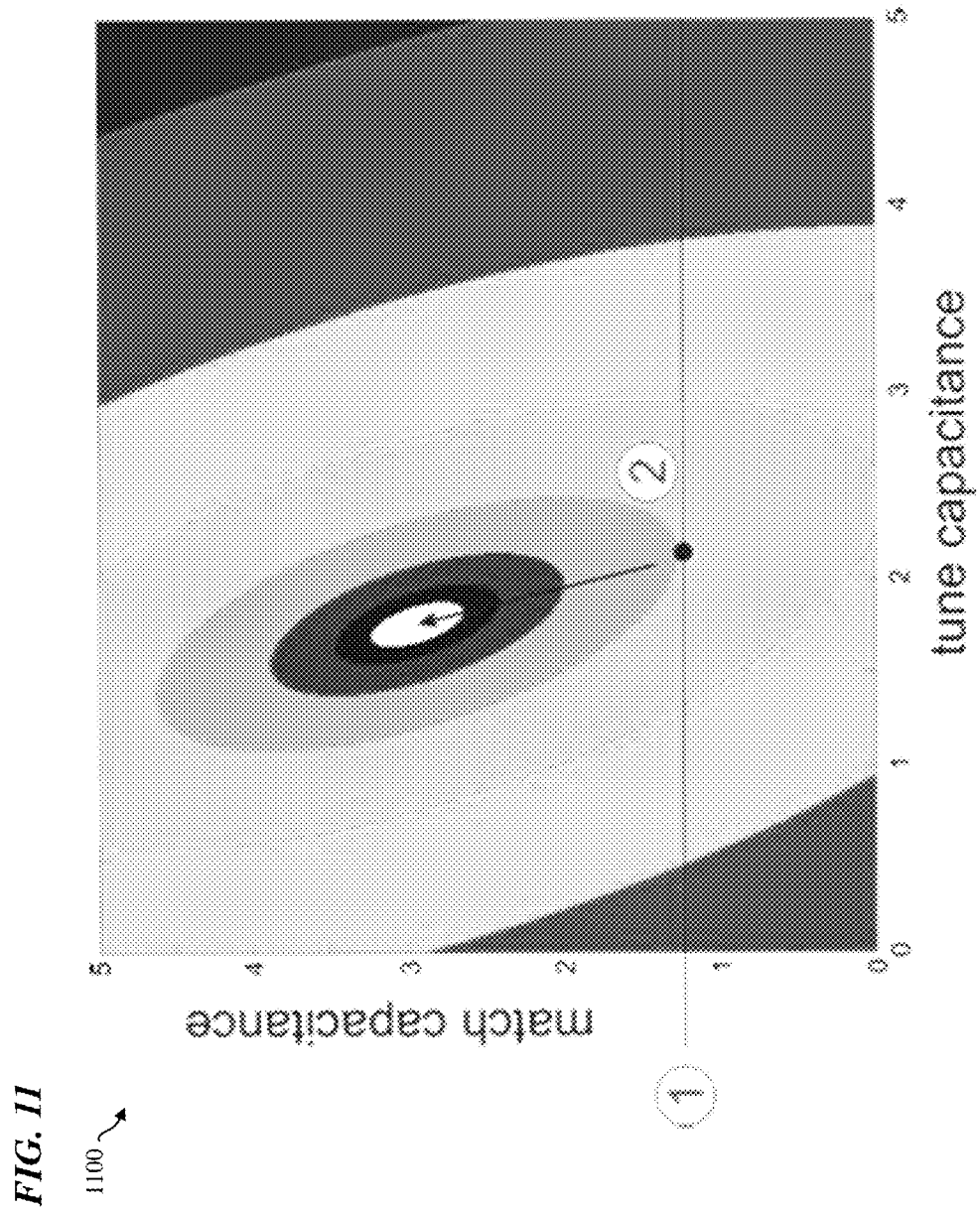
FIG. 11 shows a schematic contour plot of reflected RF power as a function of adjusting capacitance to tune and match impedance for a single coil element.

The following algorithm, illustrated in FIG. 11 (which shows a schematic contour plot of reflected RF power as a function of tune and match capacitances for a single coil element), will perform the automatic adjustment:

1. Adjust all elements to the approximate optimal values determined during calibration.
2. Activate a single coil element for transmit and power monitoring.
3. Perform a line-search on the tune capacitance ("1" in FIG. 11) for the point of minimum reflection (23, 24).
4. Check the ratio of minimum reflected power to that at other tune capacitances. If not low enough, locate the resonance with a 2-D grid search from the calibrated optimum.
5. Begin 2-D Nelder Mead optimization ("2" in FIG. 11) to fix both match and tune of that element.
6. Repeat for all elements in turn until there is little change.
7. Except: if more than 10 iterations, or if the final reflected/forward power ratios fall above a threshold, report FAILURE and request manual input from an operator or service engineer.

Line-searches and the 2-D Nelder Mead algorithm are favorable in this situation because they do not require numerical derivatives and are highly robust in the presence of noise and uncertainties in the calibration of capacitance (Nelder J A, Mead R. *A simplex method for function minimization*. Comput J. 1965; 7(4):308-13.; Lagarias J C, Reeds J A, Wright M H, Wright P E. *Convergence properties of the Nelder-Mead simplex method in low dimensions*. Siam J Optimiz. 1998; 9(1):112-47.) (references 25, 26). Preliminary experiments performing manual tuning using a network analyzer support this approach. The algorithm will be implemented in Matlab on the host computer, allowing easy adaptations, should they be necessary.

Only the magnitude of the forward and reflected RF power is monitored by B and C in FIG. 10. If this is insufficient, the complex forward and reflected RF power will be measured using the TALES safety monitor hardware in the 16-channel parallel transmit system being installed soon by Siemens. Tune and match capacitances will be adjusted to minimize the imaginary component of the reflected RF power (Venook R D, Hargreaves B A, Gold G E, Conolly S M, Scott G C. *Automatic tuning of flexible interventional RF receiver coils*. Magn Reson Med. 2005; 54(4):983-93, Hoult D I, Tomanek B. *Use of mutually inductive coupling in probe design*. Concepts in Magnetic Resonance. 2002; 15(4):262-85.) (references 19, 27). If, unlike in high-resolution NMR (Hwang F, Hoult D I. *Automatic probe tuning and matching*. Magn Reson Med. 1998; 39(2):214-22.) (reference 28), measurements are required at frequencies other than the Larmor frequency, we would insert a second pair of directional couplers between B and D in FIG. 10 and use a separate signal generator to probe the coil.

Figure 13:
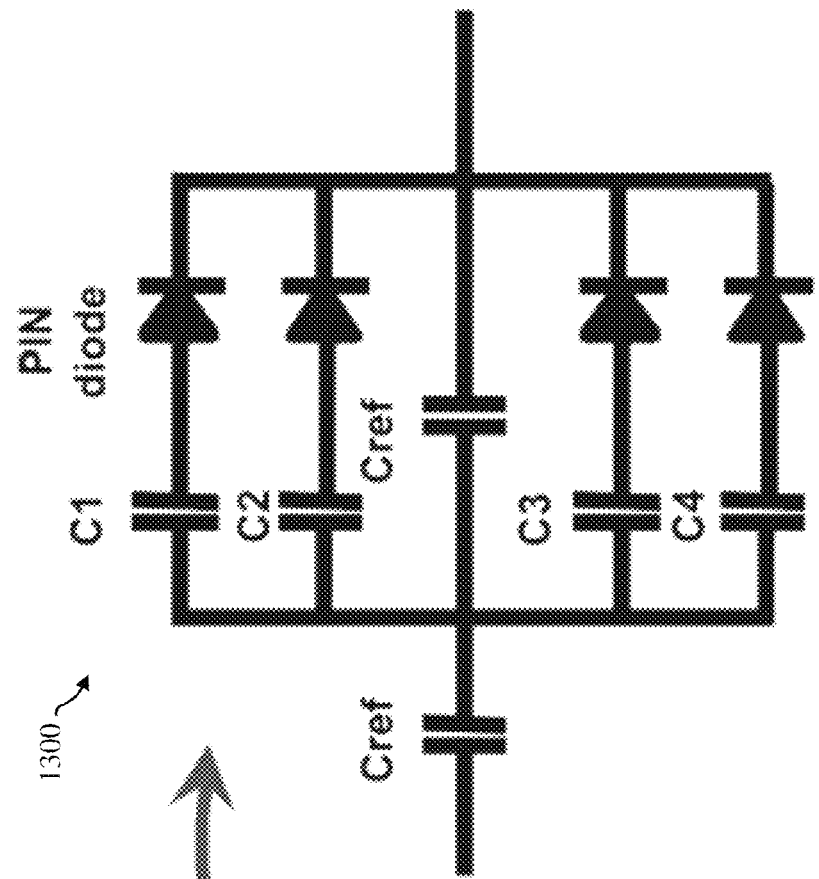
FIG. 13 shows a capacitor bank approach.
Figure 12:
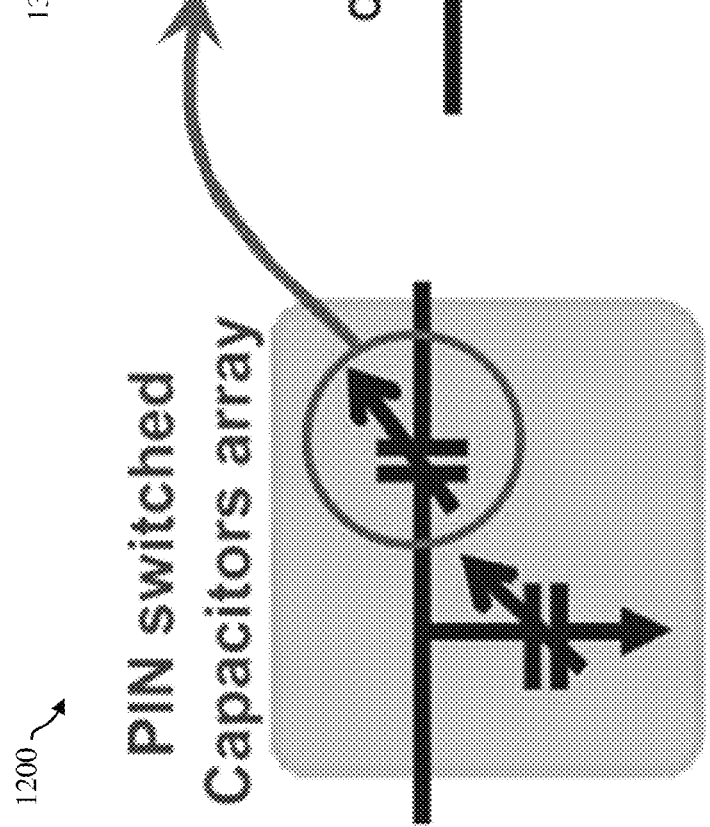
FIG. 12 shows a schematic of an array of PIN-switched capacitors.

As an alternative approach for electronic tuning and matching if the piezo-motor approach proves sub-optimal for yet unknown reasons, we will construct a transmit coil containing a bank of capacitors switched by high-power PIN diodes for the tuning and matching in place of the piezoelectric actuators in (D). Replacing the microcontroller circuit (E) with one that switches combinations of these capacitors will yield another realization of the automatically tuneable transmit coil. See FIG. 13, which shows this capacitor-bank approach.

With the auto-tuned TEM transceiver coil completed it is implemented, tested and evaluated by the methods of Coil #1 (FIG. 8) of Embodiment 1 above.

3. Auto-Tuned, 16-Channel Transmit Coil with Integrated 32-Channel Receiver.

Figure 14:
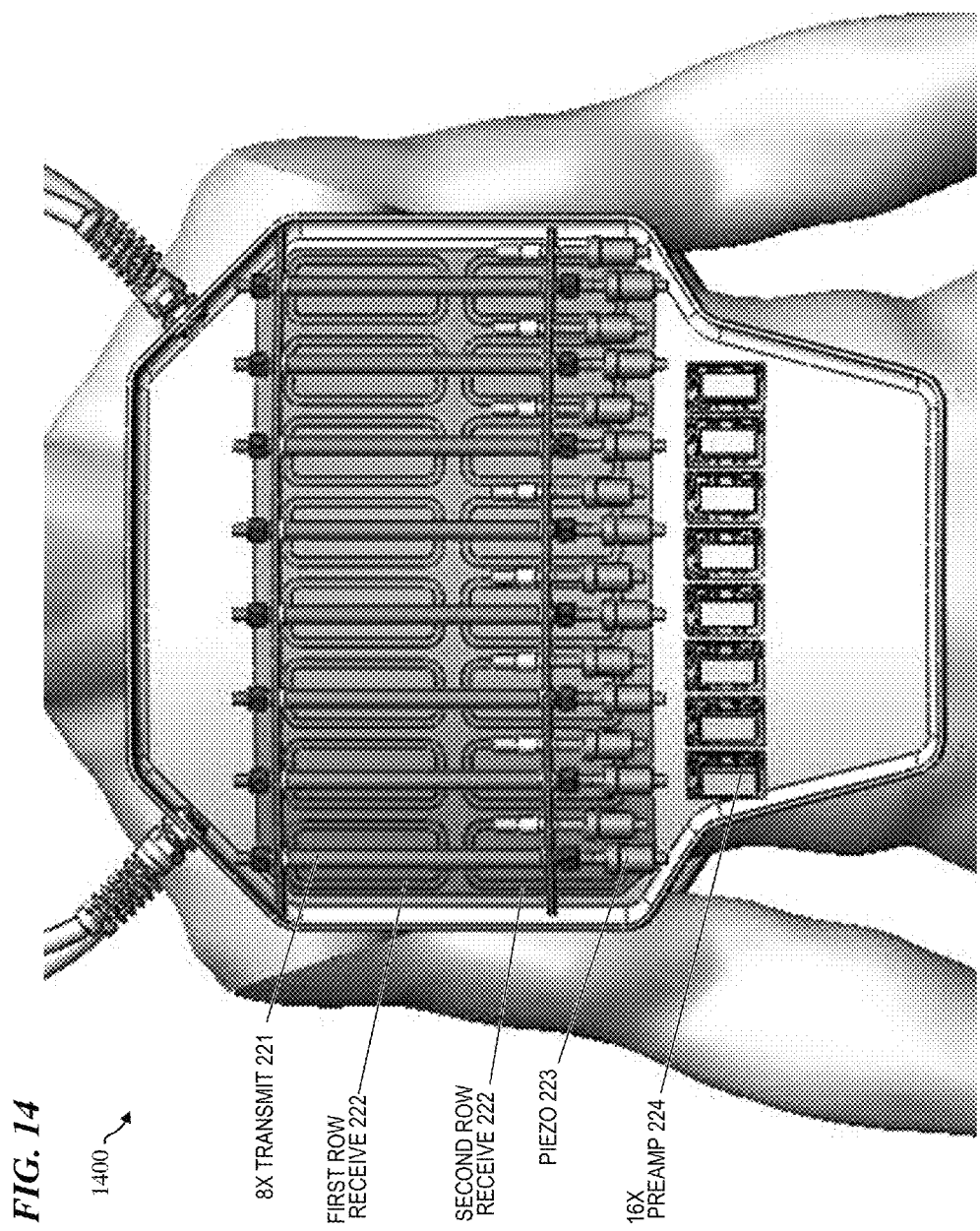
FIG. 14 shows the Best Cardiac MRI Coil, including 16 auto-tuned, shielded, shield-capacitance decoupled, transmit channels with $B_1$ shimming control, and 32 close-fitting, decoupled receiver channels, in a stable, sealed, ergonomic package.

The ultimate coil envisioned for cardiac MRI is comprised of 16 auto-tuned transmit channels, combined with 32 receiver channels. This coil takes full advantage of our 7-T system with 16 power amplifiers and 32 receivers. This configuration should give us best transmit efficiency and control, together with best receiver sensitivity and parallel-imaging performance. More specifically, the auto-tuned transmit coil will be identical in form and function to the one developed in Embodiment 2, but without the T/R switches and preamps. Instead the 32-channel receiver array will consist of a pair of 2×8 arrays, fit on the inside of respective halves of the transmit coil pair. FIG. 14 shows the anterior half of the TEM transmit array mated with the anterior half of the receive array, in position on the chest. The actively detuned receiver array is composed of loop coil elements, PIN diode detuning circuits and drivers, impedance-transformation elements, and one or more channels each containing PIN limiters, preamplifiers and multi-channel digital receivers. The cardiac receive coil array system will consist of a pair of 16-element arrays of 8-cm-diameter coil loop elements. An active PIN diode trap tuned to the proton frequency detunes each array element during transmission (Edelstein, 1986 #419). The array elements are etched on flexible circuit board and placed within the molded formers between the transmit elements and the body. The arrays must also be spaced 3 cm above high-impedance VCG leads, which in turn must be routed for minimal coupling with coil. In addition to SNR benefits, the smaller receiver coil elements minimize the effects of subject load changes. Baluns in the coaxial RF signal lines from the array elements attenuate sheath currents due to unbalanced receiver coils and load-dependent coupling between the coil elements. The individual coil array elements are electrically isolated from one another by adjusting the inductive overlap of adjacent coils to a mutual null. Coupling between coils is further minimized by using a low-noise preamplifier and a transforming network between coil output circuitry and preamplifier. The isolation between the transmit and receive coil will be bench tested for the design goal of at least 35 dB, which has been achieved.

Design, test and evaluation steps for this coil will follow those laid down for Coil #1.

FIG. 14 shows the best cardiac MRI coil, including 16 auto-tuned, shielded, shield-capacitance decoupled, transmit channels with $B_1$ shimming control, and 32 close-fitting, decoupled receiver channels, in a stable, sealed, ergonomic package.

4. Auto-Tuned, Multinuclear Transceiver Coil.

In order for $^{31}P$ spectroscopic data to be acquired in the human heart, a novel dual-tuned coil is necessary. Using the optimized transceiver design from Embodiment 1 and the automated tune and match strategy from Embodiment 2, eight "even" TEM elements will be tuned to the $^1H$ Larmor frequency (300 MHz) and eight "odd" elements will be tuned to the $^{31}P$ frequency of 120 MHz at 7 T. Dual-tuned TEM volume coils have been demonstrated by the inventor before, but never for a surface array, never with multi-channel drive, never with electronic tuning, and never at 7T. The innovative shield-capacitance decoupling method will be employed and especially useful for achieving the high degree of isolation required to separate $^1H$ channels from $^{31}P$ channels. To auto-tune this coil, the methods from Coil #2 (FIG. 9) will be followed. Other than tuning this coil to operate simultaneously at two frequencies, its design, bench test, safety test, implementation and evaluation in the magnet on humans will follow the methods of Coil 1. However, by halving the number of transmit and receive elements in this transceiver design, the $B_1$ efficiency and receive sensitivity will not equal the performance of the single-tuned coils above. While this coil is expected to be useful, it is then transformed into the following coil of Embodiment 5.

5. Auto-Tuned, Multinuclear Transmit Coil with Integrated Receiver.

This coil builds on and incorporates features of all four previous coils, and adds one feature, a dual-tuned 32-channel receiver array. The receiver array is designed along the same principles as the $^1H$ receiver array in Embodiment 3 and planned to be implemented on the array designed in Embodiment 4. There are other options still being considered for this coil. In some embodiments, we combine a full 16-channel TEM proton coil together with a single-channel 120-MHz $^{31}P$ transmitter of possibly birdcage design to preserve full power for both nuclei. In some embodiments, a surplus 3-T power amp can be found cheaply, and tweaked for service as a $^{31}P$ amplifier. If proton decoupling were not a requirement and $^1H$ and $^{31}P$ transmit could be interleaved in time, it is possible to use a PIN-switched capacitor scheme to tune 16 channels between 300- and 120 MHz by a process the military calls "frequency hopping." This auto-tuned, multinuclear coil with integrated dual-tuned receiver array will definitely be the most complicated coil. But with the advent of a powerful new 7-T human spectroscopy machine, it may prove to be the most valuable.

As the $B_1^+$ shimming example in FIG. 3 showed, some shimming is required to get any signal from all parts of the heart, but better shims produce better images. Further improvements in $B_1^+$ shim methodologies have improved image quality and reduced SAR.

These improvements have been incorporated into a study that compares standard clinical cardiac applications, like ejection fraction as measured by FLASH (fast low-angle shot MRI) and TrueFISP (true fast imaging with steady-state precession), at 1.5 T, 3 T and 7 T on the same volunteer. An example of short-axis cine on the same volunteer at the three field strengths is shown in FIG. 15. (FIG. 15 shows short-axis cine, FLASH and bSSFP, collected on the same volunteer at 1.5 T, 3 T, and 7 T.)

Figure 16A:
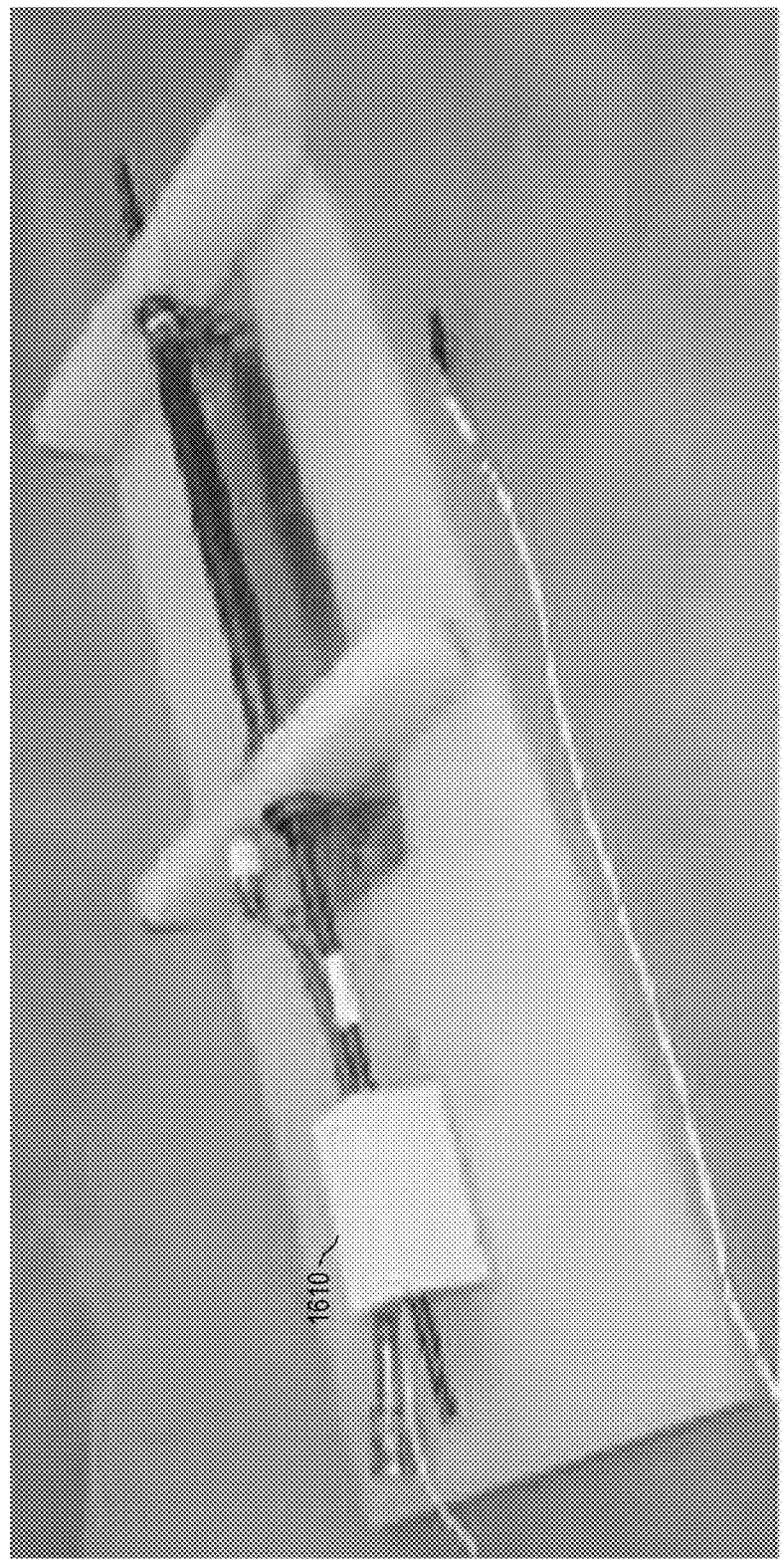
FIG. 16A is a photograph of an adjustable transmit element and FIG. 16B is a frequency response graph that shows proof of concept for remote piezoelectric tuning of transceive coils.
Figure 16B:
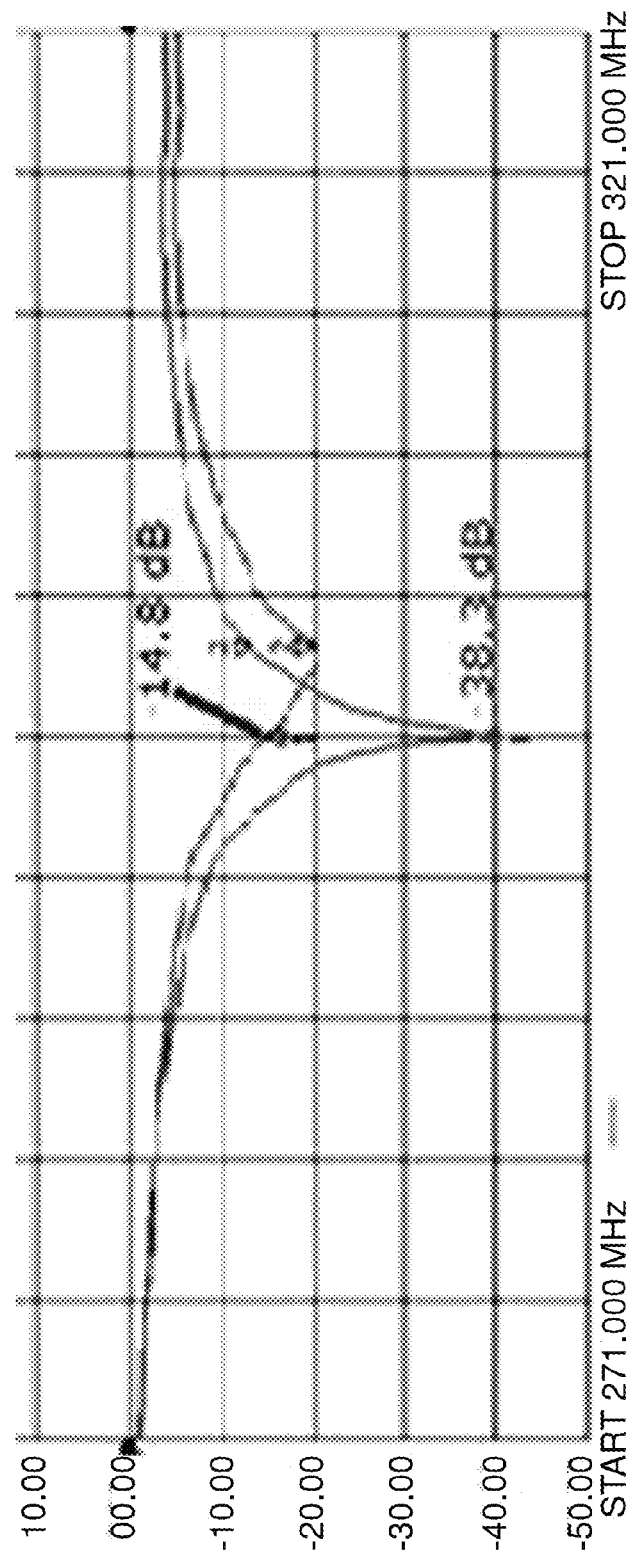

FIG. 16A shows a simple RF coil coupled to a piezoelectric motor. The plots from a network analyzer show what fraction of power is reflected from the coil over a range of frequencies. The two plots represent the before and after spectra of remote tuning the coil to the phantom in the magnet. The deeper "dip" shows a more efficient power transfer from the coil to the phantom for the Larmor frequency at 296.8 MHz. The presence of a piezoelectric motor did not affect the images acquired with the coil. FIG. 16A shows proof of concept for remote piezoelectric tuning of transceive coils.

According to the National Heart Lung and Blood Institute, more Americans die from cardiovascular diseases than any other cause. Approximately 25% of all Americans have one or more cardiovascular diseases. Highly sensitive detection is critical to biomedical science, and to diagnoses and successful treatments for these diseases. MRI/MRS at 7 T has great potential for imaging and spectroscopic detection of cardiovascular diseases. While forty 7-T MRI systems are installed in luminary labs around the world, there are currently no means available for practical 7-T cardiac MRI and MRS. This problem is solved by developing the new technology and methods required. A progressive series of five new coils is described. The first coil solves problems of transmit-field inefficiency and inhomogeneity for heart and body imaging, with a close-fitting, 16-channel TEM conformal array design with efficient shield-capacitance decoupling. The second coil progresses directly from the first with automatic tuning and matching, an innovation of huge importance for multi-channel transmit coils. The third coil combines the second, auto-tuned multi-channel transmitter with a 32-channel receiver for best transmit efficiency, control, receive sensitivity and parallel imaging performance. The final two coils extend the innovative technology of the first three coils to multi-nuclear ($^{31}$P—$^1$H) designs to make practical human cardiac imaging and spectroscopy possible for the first time at 7 T.

Currently, in forty luminary labs around the world 7-T MR is proving to be a powerful instrument for imaging the human brain. While the same potential exists for cardiac imaging at 7 T, the radio-frequency coil technology and methods critical to realizing this potential have yet to be developed. The present innovations transform the 7-T MRI system into a powerful tool for cardiac imaging and spectroscopy.

BIBLIOGRAPHY & REFERENCES CITED

1. Wiesinger F, Van de Moortele P F, Adriany G, De Zanche N, Uğurbil K, Pruessmann K P. Potential and feasibility of parallel MRI at high field. NMR Biomed. 2006; 19(3): 368-78.
2. Shrivastava D, Hanson T, Kulesa J, DelaBarre L, Iaizzo P, Vaughan J T. Radio frequency heating at 9.4T (400.2 MHz): in vivo thermoregulatory temperature response in swine. Magn Reson Med. 2009; 62(4):888-95. PMCID: PMC2782895.
3. Shrivastava D, Hanson T, Schlentz R, Gallaghar W, Snyder C, DelaBarre L, Prakash S, Iaizzo P, Vaughan J T. Radiofrequency heating at 9.4T: In vivo temperature measurement results in swine. Magn Reson Med. 2008; 59(1):73-8. PMCID: PMC2754718.
4. Vaughan J T, Snyder C J, DelaBarre L J, Bolan P J, Tian J, Bolinger L, Adriany G, Andersen P, Strupp J, Uğurbil K. Whole-body imaging at 7T: Preliminary results. Magn Reson Med. 2009; 61(1):244-8. PMCID: PMC2875945.
5. DelaBarre L, Snyder C, Van de Moortele P-F, Akgun C, Uğurbil K, Vaughan J T, editors. Cardiac Imaging at 7T. Proceedings 15th Scientific Mtg, Intl Soc for Magn Reson in Medicine; 2007 May 19-25, 2007; Berlin, Del.
6. DelaBarre L, Weale P, Snyder C, Van de Moortele P, Metzger G, Zuehlsdorff S, Nielles-Vallespin S, Bolan P J, Auerbach E, Uğurbil K, Jerecic R, Vaughan J T, editors. Cardiac Cine: Advances at 7T. Proceedings 17th Scientific Meeting, International Society for Magnetic Resonance in Medicine; 2009 April; Honolulu.
7. Snyder C J, DelaBarre L, Metzger G J, Van de Moortele P F, Akgun C, Uğurbil K, Vaughan J T. Initial results of cardiac imaging at 7 Tesla. Magn Reson Med. 2009; 61(3):517-24. PMCID: In Process.
8. van Elderen S G, Versluis M J, Webb A G, Westenberg J J, Doornbos J, Smith N B, de Roos A, Stuber M. Initial results on in vivo human coronary MR angiography at 7 T. Magn Reson Med. 2009; 62(6):1379-84.
9. Maderwald S, Orzada S, Schafer L, Bitz A, Brote I, Kraff O, et al., editors. 7T Human in vivo Cardiac Imaging with an 8-Channel Transmit/Receive Array. Proceedings 17th Scientific Meeting, International Society for Magnetic Resonance in Medicine; 2009 April; Honolulu.
10. Van de Moortele P, Snyder C, DelaBarre L, Akgun C, Wu X, Vaughan J T, et al., editors. Fast Mapping of Relative B1+Phase in the Human Head at 9.4 Tesla with a 14 Channel Transceive Coil Array. 2006 Feb. 16-18; Wuerzburg, Del.
11. Van de Moortele P F, Akgun C, Adriany G, Moeller S, Ritter J, Collins C M, Smith M B, Vaughan J T, Uğurbil K. B1 destructive interferences and spatial phase patterns at 7 T with a head transceiver array coil. Magn Reson Med. 2005; 54(6):1503-18.
12. Vaughan T, DelaBarre L, Snyder C, Tian J, Akgun C, Shrivastava D, Liu W, Olson C, Adriany G, Strupp J, Andersen P, Gopinath A, van de Moortele P F, Garwood M, Uğurbil K. 9.4T Human MRI: Preliminary Results. Magn Reson Med. 2006; 56(6):1274-82.
13. Vaughan J, Adriany G, Snyder C, Tian J, Thiel T, Bolinger L, Liu H, DelaBarre L, Uğurbil K. Efficient high-frequency body coil for high-field MRI. Magn Reson Med. 2004; 52:851-9.
14. Vaughan J, Snyder C, DelaBarre L, Tian J, Adriany G, Andersen P, Strupp J, Uğurbil K, editors. Clinical Imaging at 7T with a 16 Channel Whole Body Coil and 32 Receive Channels. Proceedings 17th Scientific Meeting, International Society for Magnetic Resonance in Medicine; 2009 April; Honolulu.
15. Metzger G J, Snyder C, Akgun C, Vaughan T, Uğurbil K, Van de Moortele P F. Local B1+ shimming for prostate imaging with transceiver arrays at 7T based on subject-dependent transmit phase measurements. Magn Reson Med. 2008; 59(2):396-409.
16. van den Bergen B, van den Berg C A, Klomp D W, Lagendijk J J. SAR and power implications of different RF shimming strategies in the pelvis for 7T MRI. J Magn Reson Imaging. 2009; 30(1):194-202.
17. van den Bergen B, van den Berg C A, Bartels L W, Lagendijk J J. 7 T body MRI: B1 shimming with simultaneous SAR reduction. Phys Med Biol. 2007; 52(17): 5429-41.
18. de Alejo R P, Garrido C, Villa P, Rodriguez I, Vaquero J J, Ruiz-Cabello J, Cortijo M. Automatic tuning and matching of a small multifrequency saddle coil at 4.7 T. Magn Reson Med. 2004; 51(4):869-73.
19. Venook R D, Hargreaves B A, Gold G E, Conolly S M, Scott G C. Automatic tuning of flexible interventional RF receiver coils. Magn Reson Med. 2005; 54(4):983-93.
20. Cho Y K, Merkle H, Zhang J, Tsekos N V, Bache R J, Uğurbil K. Noninvasive measurements of transmural myocardial metabolites using 3-D (31)P NMR spectroscopy. Am J Physiology. 2001; 280(1):H489-97.
21. Hudsmith L E, Neubauer S. Magnetic resonance spectroscopy in myocardial disease. JACC Cardiovasc Imaging. 2009; 2(1):87-96.
22. Turowski S G, Seshadri M, Loecher M, Podniesinski E, Spernyak J A, Mazurchuk R V. Performance of a novel piezoelectric motor at 4.7 T: applications and initial tests. Magn Reson Imaging. 2008; 26(3):426-32.
23. Hyde J S, Rilling R J, Jesmanowicz A, Kneeland J B. Piezoelectric-Controlled Tuning Capacitor for Surface Coils. Magn Reson Med. 1989; 12(1):50-5.

24. Muftuler L T, Gulsen G, Sezen K D, Nalcioglu 0. Automatic tuned MRI RF coil for multinuclear imaging of small animals at 3T. J Magn Reson. 2002; 155(1):39-44.
25. Nelder J A, Mead R. A simplex method for function minimization. Comput J. 1965; 7(4):308-13.
26. Lagarias J C, Reeds J A, Wright M H, Wright P E. Convergence properties of the Nelder-Mead simplex method in low dimensions. Siam J Optimiz. 1998; 9(1): 112-47.
27. Hoult D I, Tomanek B. Use of mutually inductive coupling in probe design. Concepts in Magnetic Resonance. 2002; 15(4):262-85.
28. Hwang F, Hoult D I. Automatic probe tuning and matching. Magn Reson Med. 1998; 39(2):214-22.
29. Dewhirst M W, Viglianti B L, Lora-Michiels M, Hanson M, Hoopes P J. Basic principles of thermal dosimetry and thermal thresholds for tissue damage from hyperthermia. Int J Hyperthermia. 2003; 19(3):267-94.
30. Mount L E. Adaptation to thermal environment: man and his productive animals/Laurence E. Mount. EJW B, AJ W, MA S, editors. Baltimore: University Park Press; 1979.
31. Pennes, HH Analysis of tissue and arterial blood temperature in the resting human forearm. J. Appl. Physiol. 1: 93-122, 1948
32. Insko E K, Leigh J S. A double descrete cosine quadrature coil design. J Magn Reson 1993; 89:41-50
33. Kellman P, McVeigh E R. Image reconstruction in SNR units: a general method for SNR measurement. Magnetic resonance in medicine 2005; 54(6):1439-47.
34. Cunningham C H, Pauly J M, Nayak K S. Saturated double-angle method for rapid B1+ mapping. Magnetic Resonance in Medicine 2006; 55(6):1326-1333
35. Sung K, Nayak K S. Measurement and Characterization of RF Non-Uniformity over the Heart at 3T Using Body Coil Transmission. Journal of Magnetic Resonance Imaging. 2008; 27(3):643-648.
36. Sung K, Nayak K S. B1+Compensation in 3T Cardiac Imaging Using Short 2DRF Pulses. Magnetic Resonance in Medicine 2008; 59(3):441-446.
37. Sung K, Nayak K S. The Design and Use of Tailored Hard-Pulse Trains for Uniform Saturation of Myocardium at 3 Tesla. Magnetic Resonance in Medicine 2008; 60(4): 997-1002
38. Edelstein W A, Glover G H, Hardy C J, Redington R W. The Intrinsic Signal-to-Noise Ratio in NMR Imaging. Magnetic Resonance in Medicine 1986; 3:604-618

In some embodiments, the present invention provides an apparatus that includes a coil for operation in a magnetic-resonance machine that operates at magnetic fields of at least 7 tesla, the coil including: a plurality of coil elements, a plurality of transmit-receive circuits, a plurality non-magnetic circuit elements that are tunable, a plurality of actuators operatively coupled to the tunable non-magnetic circuit elements, and a controller operatively coupled to control the actuators to automatically tune resonance frequency and match impedance of each of the plurality of circuit elements.

In some embodiments of the apparatus, each one of the plurality of circuit elements is a mechanically tunable capacitor. In some embodiments, the plurality of circuit elements includes capacitors. In some embodiments, the plurality of circuit elements includes mechanically tunable inductance.

In some embodiments, the plurality of coil elements includes a plurality of transmit elements, and wherein the plurality of circuit elements include a variable capacitor in series with each of the plurality of transmit elements and a variable capacitor in parallel with each of the plurality of transmit elements. In some embodiments, the plurality of coil elements includes a plurality of transmit elements, and the plurality of circuit elements include a mechanically tunable capacitor in series with each of the plurality of transmit elements and a mechanically tunable capacitor in parallel with each of the plurality of transmit elements.

In some embodiments, the plurality of coil elements includes a plurality of transmit elements, and wherein the plurality of circuit elements include a mechanically tunable inductance in each of the plurality of transmit elements.

In some embodiments, the present invention provides a computer implemented method that includes providing a magnetic-resonance coil for operation at a field strength of at least seven tesla, the coil having a plurality of coil elements; setting each of the plurality of coil elements to approximate optimal values determined during a prior calibration; activating an Nth single coil element for transmit and power monitoring; varying a tune capacitance for a point of minimum reflection; checking a ratio of minimum reflected power to that at other tune capacitances; if the ratio is not low enough to meet a predetermined criterion, performing a two-dimensional grid search from the calibrated optimal values to locate a resonance; adjusting both an impedance match and tuning match of the Nth single coil element using a two-dimensional Nelder-Mead optimization of the Nth element; and repeating the activating, varying, checking, performing, and adjusting for each of the plurality of coil elements in turn until an amount of change at each coil element is below a predetermined criterion change amount.

In some embodiments, the method further includes if after more than 10 iterations, or if a final reflected/forward power ratio falls above a threshold, report a FAILURE and request manual input from an operator or service engineer.

In some embodiments of the method, the adjusting includes mechanically adjusting. In some embodiments, the method further includes providing a plurality of mechanically tunable capacitors, wherein the mechanically adjusting is performed using at least the plurality of mechanically tunable capacitors. In some embodiments, the method further includes providing mechanically tunable inductance, wherein the mechanically adjusting is performed using at least the mechanically tunable inductance. In some embodiments, the method further includes providing a plurality of capacitors, wherein the adjusting is performed using at least the plurality of capacitors.

In some embodiments of the method, the plurality of coil elements includes a plurality of transmit elements, the method further including connecting a variable capacitor in series with each of the plurality of transmit elements and connecting a variable capacitor in parallel with each of the plurality of transmit elements, wherein the adjusting is performed using at least the variable capacitors connected in series and the variable capacitors connected in parallel.

In some embodiments, the present invention provides an apparatus that includes a magnetic-resonance coil for operation at a field strength of at least seven tesla, the coil having a plurality of coil elements; means for setting each of the plurality of coil elements to approximate optimal values determined during a prior calibration; means for activating an Nth single coil element for transmit and power monitoring; means for varying a tune capacitance for a point of minimum reflection; means for checking a ratio of minimum reflected power to that at other tune capacitances; if the ratio is not low enough to meet a predetermined criterion, means for performing a two-dimensional grid search from the calibrated optimal values to locate a resonance; means for adjusting both an impedance match and tuning match of the Nth single coil element; and means for repeatedly operating the means for activating, means for varying, means for checking, means for performing, and means for adjusting for each of the plurality of coil elements in turn until the amount of change at each coil element is below a predetermined criterion change amount.

In some embodiments of the apparatus, the means for adjusting includes means for mechanically adjusting. In some embodiments, the means for mechanically adjusting includes a plurality of mechanically tunable capacitors. In some embodiments, the means for mechanically adjusting includes mechanically tunable inductance. In some embodiments, the means for adjusting includes a plurality of capacitors. In some embodiments, the plurality of coil elements includes a plurality of transmit elements, wherein the apparatus further includes a variable capacitor connected in series with each of the plurality of transmit elements; and a variable capacitor connected in parallel with each of the plurality of transmit elements.

In some embodiments, the present invention provides a computer-readable medium having instructions stored thereon for causing a suitably programmed information processor to execute a method that includes setting a plurality of coil elements to approximate optimal values determined during a prior calibration; activating an Nth single coil for transmit and power monitoring; performing a line-search on the tune capacitance for a point of minimum reflection; checking a ratio of minimum reflected power to that at other tune capacitances; if the ratio is not low enough to meet a predetermined criterion, performing a two-dimensional grid search from the calibrated optimum to locate a resonance; adjusting both an impedance match and tuning match of the Nth single coil using a two-dimensional Nelder-Mead optimization of the Nth element; and repeating for all of the plurality of elements in turn until the amount of change is below a predetermined criterion.

In some embodiments, the present invention provides a computer-readable medium having instructions stored thereon for causing a suitably programmed information processor to execute a method that includes setting each of a plurality of coil elements to approximate optimal values determined during a prior calibration; activating an Nth single coil element for transmit and power monitoring; varying a tune capacitance for a point of minimum reflection; checking a ratio of minimum reflected power to that at other tune capacitances; if the ratio is not low enough to meet a predetermined criterion, performing a two-dimensional grid search from the calibrated optimal values to locate a resonance; adjusting both an impedance match and tuning match of the Nth single coil element using a two-dimensional Nelder-Mead optimization of the Nth element; and repeating the activating, varying, checking, performing, and adjusting for each of the plurality of coil elements in turn until an amount of change at each coil element is below a predetermined criterion change amount.

In some embodiments, the computer-readable medium further includes instructions such that the method further includes if after more than 10 iterations, or if a final reflected/forward power ratio falls above a threshold, report a FAILURE and request manual input from an operator or service engineer. In some embodiments, the computer-readable medium further includes instructions such that the adjusting includes mechanically adjusting. In some embodiments, the computer-readable medium further includes instructions such that the method further includes performing the mechanically adjusting using at least a plurality of mechanically tunable capacitors.

In some embodiments, the computer-readable medium, further includes instructions such that the method further includes performing the mechanically adjusting using at least mechanically tunable inductance. In some embodiments, the computer-readable medium further includes instructions such that the method further includes performing the adjusting using at least a plurality of capacitors. In some embodiments, the computer-readable medium further includes instructions such that the method further includes performing the adjusting using at least a variable capacitor connected in parallel to each of the plurality of coil elements and a variable capacitor connected in series to each of the plurality of coil elements.

In some embodiments, the present invention provides an apparatus that includes a coil for operation in an magnetic-resonance machine that operates at magnetic fields of at least 7 tesla, the coil including: a plurality of coil elements, a plurality of transmit-receive circuits, a plurality non-magnetic circuit elements that are tunable, wherein the plurality non-magnetic circuit elements are connected to the plurality of coil elements, a plurality of actuators operatively coupled to the tunable non-magnetic circuit elements, and a controller operatively coupled to control the actuators to automatically tune resonance frequency and match impedance of each of the plurality of coil elements. In some embodiments, each one of the plurality of circuit elements is a mechanically tunable capacitor. In some embodiments, the plurality of coil elements that the controller automatically tunes the resonance frequency of and matches the impedance of includes both transmit elements and receive elements. In some embodiments, the plurality of circuit elements includes mechanically tunable inductance. In some embodiments, the plurality of coil elements includes a plurality of transmit elements, and wherein the plurality of circuit elements include a variable capacitor in series with each of the plurality of transmit elements and a variable capacitor in parallel with each of the plurality of transmit elements. In some embodiments, the plurality of coil elements includes a plurality of transmit elements, and wherein the plurality of circuit elements include a mechanically tunable capacitor in series with each of the plurality of transmit elements and a mechanically tunable capacitor in parallel with each of the plurality of transmit elements. In some embodiments, the plurality of coil elements includes a plurality of transmit elements, and wherein the plurality of circuit elements include a mechanically tunable inductance in each of the plurality of transmit elements.

In some embodiments, the present invention provides a method that includes the following ALGORITHM: providing a magnetic-resonance coil for operation at a field strength of at least seven tesla, the coil having a plurality of coil elements; setting each of the plurality of coil elements to approximate optimal values determined during a prior calibration; activating an Nth single coil element for transmit and power monitoring; varying a tune capacitance for a point of minimum reflection; checking a ratio of minimum reflected power to that at other tune capacitances; if the ratio is not low enough to meet a predetermined criterion, performing a two-dimensional grid search from the calibrated optimal values to locate a resonance; adjusting both an impedance match and tuning match of the Nth single coil element using a two-dimensional Nelder-Mead optimization of the Nth element; and repeating the activating, varying, checking, performing, and adjusting for each of the plurality of coil elements in turn until an amount of change at every coil element is below a predetermined criterion change amount.

Some embodiments further include: if either more than 10 iterations have occurred without going below the predetermined criterion change amount at every coil element, or if a final reflected/forward power ratio falls above a threshold, report a FAILURE and request manual input from an operator.

In some embodiments, the adjusting includes mechanically adjusting capacitances to tune resonance frequencies and match impedances.

In some embodiments, the Nth coil element is a receive element, and wherein the adjusting of both the impedance match and the resonance frequency of the Nth coil element adjusts the receive characteristics of the Nth single coil element, and wherein a N+1st coil element is a transmit element, and wherein the adjusting of both the impedance match and the resonance frequency of the N+1st single coil element adjusts the transmit characteristics of the N+1st coil element.

Some embodiments further include providing mechanically tunable inductance, wherein the adjusting includes mechanically tuning the inductance.

Some embodiments further include providing a plurality of capacitors, wherein the adjusting is performed by varying a capacitance of the plurality of capacitors.

In some embodiments, the plurality of coil elements includes a plurality of transmit elements, and the method further includes connecting a variable capacitor in series with each of the plurality of transmit elements and connecting a variable capacitor in parallel with each of the plurality of transmit elements, wherein the adjusting is performed using at least the variable capacitors connected in series and the variable capacitors connected in parallel.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
a coil for operation in a magnetic-resonance machine that operates at a given magnetic field strength, the coil including:
a plurality of coil elements,
a plurality of inner shield elements,
a plurality of transmit-receive circuits, wherein each one of the plurality of transmit-receive circuits includes a respective transmit amplifier operatively coupled through a first respective non-magnetic variable capacitance to its respective one of the plurality of coil elements, and wherein each one respective of the plurality of inner shield elements is operatively coupled through a second respective non-magnetic variable capacitance to its respective one of the plurality of coil elements; and
a computer operatively coupled to control a capacitance value of each one of the first respective non-magnetic variable capacitances, and to control a capacitance value of each one of the second respective non-magnetic variable capacitances to automatically tune resonance frequency and match impedance of each of the plurality of coil elements.

2. The apparatus of claim 1, further comprising a plurality of outer shield elements, wherein each one of the plurality of outer shield elements overlaps two of the plurality of inner shield elements.

3. The apparatus of claim 1, wherein the plurality of coil elements that the computer automatically tunes the resonance frequency of and matches the impedance of includes both transmit elements and receive elements.

4. The apparatus of claim 1, wherein the plurality of circuit elements includes mechanically tunable inductance.

5. The apparatus of claim 1, wherein each first respective non-magnetic variable capacitance of the plurality of transmit-receive circuits includes a mechanically tunable capacitor in series with its respective transmit one of the plurality of coil elements, and wherein the computer causes a mechanical tuning of each first respective variable capacitance of the plurality of transmit-receive circuits.

6. The apparatus of claim 1, wherein the plurality of coil elements includes a plurality of transmit elements, and wherein each of the plurality of transmit-receive circuits includes a mechanically tunable inductance in each of the plurality of transmit elements.

7. The apparatus of claim 1, wherein the plurality of coil elements includes a plurality of coaxial TEM coil elements, wherein each coaxial TEM coil element includes an inner conductor and an outer conductor that are movable lengthwise relative to one another, and wherein the computer causes a mechanical lengthwise position adjustment of each respective inner conductor and outer conductor position relative to one another for each respective one of the plurality of coaxial TEM coil elements.

8. The apparatus of claim 1, wherein the given magnetic-field strength at which the coil operates is at least seven tesla.

9. A computer implemented method comprising:
providing a coil for operation in a magnetic-resonance machine that operates at a given magnetic field strength, the coil including a plurality of N coil elements, a plurality of N inner shield elements, and a plurality of N transmit-receive circuits, wherein each one of the plurality of N transmit-receive circuits includes a respective transmit amplifier operatively coupled through a first respective non-magnetic variable capacitance to its respective one of the plurality of N coil elements, wherein each respective one of the plurality of N inner shield elements is operatively coupled through a second respective non-magnetic variable capacitance to its respective one of the plurality of N coil elements, and wherein N is an integer greater than one;
setting, by a computer, electrical parameters of each of the plurality of coil elements to approximate values of resonance frequency and matched impedance;
automatically adjusting, by the computer, each respective first non-magnetic variable capacitance to adjust a frequency-tuning match and automatically adjusting each respective second non-magnetic variable capacitance to adjust an impedance match of the Nth coil element;

repeating the automatically adjusting, by the computer, of the first and second respective non-magnetic variable capacitance for each of the plurality of coil elements in turn until an amount of change at every coil element is below a predetermined criterion change amount; and
obtaining a magnetic-resonance image using the magnetic-resonance coil.

10. The method of claim 9, further comprising:
providing a plurality of outer shield elements; and
positioning each one of the plurality of outer shield elements to overlap two of the plurality of inner shield elements.

11. The method of claim 9, wherein the plurality of coil elements includes both transmit elements and receive elements, and wherein the automatically adjusting each respective first non-magnetic variable capacitance is performed for both transmit and receive elements.

12. The method of claim 9, wherein each one of the plurality of circuit elements includes a mechanically tunable inductance.

13. The method of claim 9, wherein each first respective non-magnetic variable capacitance of the plurality of transmit-receive circuits includes a mechanically tunable capacitor in series with its respective transmit one of the plurality of coil elements, and wherein the automatically adjusting of each respective first non-magnetic variable capacitance includes mechanically tuning each first respective variable capacitance of the plurality of transmit-receive circuits.

14. The method of claim 9, wherein the plurality of coil elements includes a plurality of transmit elements, and wherein the method further includes mechanically tuning an inductance in each of the plurality of transmit elements.

15. The method of claim 9, wherein the plurality of coil elements includes a plurality of coaxial TEM coil elements, wherein each coaxial TEM coil element includes an inner conductor and an outer conductor that are movable lengthwise relative to one another, and wherein the method further includes mechanical adjusting lengthwise positions of each respective inner conductor and outer conductor position relative to one another for each respective one of the plurality of coaxial TEM coil elements.

16. An apparatus comprising:
a coil for operation in a magnetic-resonance machine that operates at a given magnetic field strength, the coil including:
a plurality of N coil elements,
a plurality of N inner shield elements, and
a plurality of N transmit-receive circuits, wherein each one of the plurality of N transmit-receive circuits includes a respective transmit amplifier operatively coupled through a first respective non-magnetic variable capacitance to its respective one of the plurality of N coil elements, wherein each respective one of the plurality of N inner shield elements is operatively coupled through a second respective non-magnetic variable capacitance to its respective one of the plurality of N coil elements, and wherein N is an integer greater than one;
means for setting each of the plurality of coil elements to approximate values of resonance frequency and matched impedance;
means for automatically adjusting each respective first non-magnetic variable capacitance to adjust a frequency-tuning match,
means for automatically adjusting each respective second non-magnetic variable capacitance to adjust an impedance match;
means for repeating the automatically adjusting of the first and second respective non-magnetic variable capacitance for each of the plurality of coil elements in turn until an amount of change at every coil element is below a predetermined criterion change amount; and
means for obtaining a magnetic-resonance image using the magnetic-resonance coil.

17. The apparatus of claim 16, wherein the plurality of coil elements includes both transmit elements and receive elements, and wherein the means for automatically adjusting each respective first non-magnetic variable capacitance operates on both transmit and receive elements.

18. The apparatus of claim 16, wherein each first respective non-magnetic variable capacitance of the plurality of transmit-receive circuits includes a mechanically tunable capacitor in series with its respective transmit one of the plurality of coil elements, and wherein the means for automatically adjusting of each respective first non-magnetic variable capacitance includes means for mechanically tuning each first respective variable capacitance of the plurality of transmit-receive circuits.

19. The apparatus of claim 16, wherein the plurality of coil elements includes a plurality of transmit elements, and wherein the method further includes mechanically tuning an inductance in each of the plurality of transmit elements.

20. The apparatus of claim 16, wherein the plurality of coil elements includes a plurality of coaxial TEM coil elements, wherein each coaxial TEM coil element includes an inner conductor and an outer conductor that are movable lengthwise relative to one another, and wherein the apparatus further includes means for mechanical adjusting lengthwise positions of each respective inner conductor and outer conductor position relative to one another for each respective one of the plurality of coaxial TEM coil elements.

* * * * *